United States Patent
De Villiers-Zur Hausen et al.

(10) Patent No.: US 6,413,522 B1
(45) Date of Patent: *Jul. 2, 2002

(54) PAPILLOMA VIRUSES, PRODUCTS FOR THE DETECTION THEREOF AS WELL AS FOR TREATING DISEASES CAUSED BY THEM

(75) Inventors: Ethel-Michele De Villiers-Zur Hausen; Harald Zur Hausen, both of Waldmichelbach; Donna Lavergne, Flörsheim/Dalsheim, all of (DE); Claire Benton, Edinburgh (GB)

(73) Assignee: Deutsches Krebsforschungszentrum Stiftung des Offentlichen Rechts, Heidelberg (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/319,056
(22) PCT Filed: Nov. 12, 1997
(86) PCT No.: PCT/DE97/02659
§ 371 (c)(1),
(2), (4) Date: Aug. 5, 1999
(87) PCT Pub. No.: WO98/23752
PCT Pub. Date: Jun. 4, 1998

(30) Foreign Application Priority Data

Nov. 26, 1996 (DE) .......................... 196 48 962

(51) Int. Cl.[7] .......................... A61K 39/12; C12N 1/12; C12N 15/00; C07H 21/04
(52) U.S. Cl. .................. 424/204.1; 424/199.1; 435/5; 435/69.1; 435/69.3; 435/235.1; 435/320.1; 536/23.72; 530/350; 530/324

(58) Field of Search .......................... 435/6, 701, 69.3, 435/69.1, 235.1, 320.1; 536/23.1, 23.72; 396/2, 1; 530/350, 387.1, 324; 424/204.1, 199.1

(56) References Cited

FOREIGN PATENT DOCUMENTS

WO    WO 95/30754    11/1995
WO    WO 97/04099    * 2/1997

OTHER PUBLICATIONS de Villiers et al., 1997, "Prevailing papillomaviurs types in non–melanoma carcinomas of the skin in renal allograft recipients,"*International Journal of Cancer 73*(3):356–361.

Hagensee et al., 1993, "Self–assembly of human papillomavirus type 1 capsids by expression of the L1 protein alone or by coexpression of the L1 and L2 capsid proteins," *Journal of Virology 67*(1):315–322.

Kirnbauer et al., 1993, "Effecient self–assembly of human papillomavirus type 16 L1 and L1–L2 into virus–like particles," *Journal of Virology 67*(12):6929–6936.

zur Hausen, 1977, "Human papillomavirus and their possible role in squamous cell carcinomas," *Curr. Top. Microbiol. Immunol.* 78:1–30.

zur Hausen, 1996, "Papillomavirus infections—a major cause of human cancers," *Biochimica et Biophysica Acta 1288*(2):F55–F78.

* cited by examiner

Primary Examiner—Ali R. Salimi
(74) Attorney, Agent, or Firm—Pennie & Edmonds LLP

(57) ABSTRACT

This invention relates to a DNA coding for a peptide of a papilloma virus major capsid protein and a papilloma virus genome, respectively. Furthermore, this invention concerns proteins coded by the papilloma virus genome and antibodies directed thereagainst as well as the use thereof for diagnosis, treatment and vaccination.

23 Claims, 11 Drawing Sheets

FIG. 1

DL17.seq from 1 to 416:

```
      CTCGAGGATGGGGAAATGTGCGATATTGGATTTGGAGCATGCAATTTTAAACAGTTACAG
  1   ---------+---------+---------+---------+---------+---------+  60
      GAGCTCCTACCCCTTTACACGCTATAACCTAAACCTCGTACGTTAAAATTTGTCAATGTC

L   E   D   G   E   M   C   D   I   G   F   G   A   C   N   F   K   Q   L   Q   -

AAGGATAGATCTGGTGTTCCATTAGATATAGTAGAGAGCACTTGTAAGTATCCTGATTTT
 61   ---------+---------+---------+---------+---------+---------+ 120
      TTCCTATCTAGACCACAAGGTAATCTATATCATCTCTCGTGAACATTCATAGGACTAAAA

K   D   R   S   G   V   P   L   D   I   V   E   S   T   C   K   Y   P   D   F   -

TTAAAGATGGGTAAGGATATGTATGGCGACGAGCTATTTTTCTATGGCAGACGAGAACAG
121   ---------+---------+---------+---------+---------+---------+ 180
      AATTTCTACCCATTCCTATACATACCGCTGCTCGATAAAAAGATACCGTCTGCTCTTGTC

L   K   M   G   K   D   M   Y   G   D   E   L   F   F   Y   G   R   R   E   Q   -

TTATATGTAAGACATAACTTTTCTCGTGCAGGCACTGTAGGAGATAGTATACCTTTACCT
181   ---------+---------+---------+---------+---------+---------+ 240
      AATATACATTCTGTATTGAAAAGAGCACGTCCGTGACATCCTCTATCATATGGAAATGGA

L   Y   V   R   H   N   F   S   R   A   G   T   V   G   D   S   I   P   L   P   -

GATCAGGATACTGCATTTTATAGAAGTCCTAATACTGCAAATAATGATTTGCCTCAAAAT
241   ---------+---------+---------+---------+---------+---------+ 300
      CTAGTCCTATGACGTAAAATATCTTCAGGATTATGACGTTTATTACTAAACGGAGTTTTA

D   Q   D   T   A   F   Y   R   S   P   N   T   A   N   N   D   L   P   Q   N   -

ACATTAGCGTCTCACATATACTGTGCCATCCCAAGTGGTTCTTTAACCAGTAGTGATTCT
301   ---------+---------+---------+---------+---------+---------+ 360
      TGTAATCGCAGAGTGTATATGACACGGTAGGGTTCACCAAGAAATTGGTCATCACTAAGA

T   L   A   S   H   I   Y   C   A   I   P   S   G   S   L   T   S   S   D   S   -

CAATTATTTAATAGGCCTTATTGGCTGCAAAATGCTCAGGGCACCAACAACGGCGT
361   ---------+---------+---------+---------+---------+------ 416
      GTTAATAAATTATCCGGAATAACCGACGTTTTACGAGTCCCGTGGTTGTTGCCGCA

DL20.seq from 1 to 386:

```
      ATTGAGGATGGTGATATGGTAGACATAGGATTTGGGAATTGTAATTTTAAAGCTTTACAA
  1   ---------+---------+---------+---------+---------+---------+  60
      TAACTCCTACCACTATACCATCTGTATCCTAAACCCTTAACATTAAAATTTCGAAATGTT

I  E  D  G  D  M  V  D  I  G  F  G  N  C  N  F  K  A  L  Q   -

CAGGACAAGGCTGGTACGCCTTTAGAGTTAACTAATGAAAAATGTAAGTGGCCAGATTTT
 61   ---------+---------+---------+---------+---------+---------+ 120
      GTCCTGTTCCGACCATGCGGAAATCTCAATTGATTACTTTTTACATTCACCGGTCTAAAA

Q  D  K  A  G  T  P  L  E  L  T  N  E  K  C  K  W  P  D  P   -

CTGAAGATGGAAAAAGACACTTATGGAGACCAGATGTTTTTCTGTGGCAGGAAGGAGCAA
121   ---------+---------+---------+---------+---------+---------+ 180
      GACTTCTACCTTTTTCTGTGAATACCTCTGGTCTACAAAAAGACACCGTCCTTCCTCGTT

L  K  M  E  K  D  T  Y  G  D  Q  M  F  F  C  G  R  K  E  Q   -

ATGTATTCTAGGCATATGCTTGCTAAAGCGGGTATTGATGGTGATCATATACCAGAATCA
181   ---------+---------+---------+---------+---------+---------+ 240
      TACATAAGATCCGTATACGAACGATTTCGCCCATAACTACCACTAGTATATGGTCTTAGT

M  Y  S  R  H  M  L  A  K  A  G  I  D  G  D  H  I  P  E  S   -

TTATACCATTCGCCAAAGAATAATGGAAATGGCATTGCTCCTTACACTTACTTTCCAACC
241   ---------+---------+---------+---------+---------+---------+ 300
      AATATGGTAAGCGGTTTCTTATTACCTTTACCGTAACGAGGAATGTGAATGAAAGGTTGG

L  Y  H  S  P  K  N  N  G  N  G  I  A  P  Y  T  Y  F  P  T   -

ACAAGCGGTTCCTTAGTCACAAGTGATAATCAATTATTTAACAGGCCATATTGGCTTCAT
301   ---------+---------+---------+---------+---------+---------+ 360
      TGTTCGCCAAGGAATCAGTGTTCACTATTAGTTAATAAATTGTCCGGTATAACCGAAGTA

T  S  G  S  L  V  T  S  D  N  Q  L  F  N  R  P  Y  W  L  H   -

AATTCACAAGGAACCAATAACGGTAT
361   ---------+---------+------ 386
      TTAAGTGTTCCTTGGTTATTGCCATA

DL27.seq from 1 to 410:

```
      CTGGAGGATGGCGACATGTGTGATATAGGCTTTGGAGCTTTTAACTTTAAAGCTTTGCAG
  1   ---------+---------+---------+---------+---------+---------+  60
      GACCTCCTACCGCTGTACACACTATATCCGAAACCTCGAAAATTGAAATTTCGAAACGTC

L  E  D  G  D  M  C  D  I  G  F  G  A  F  N  F  K  A  L  Q   -

GATGATAAATCCAGTGCACCATTAGATGTAGTTGGTACTTTGTGTAAATGGCCTGACTTC
 61   ---------+---------+---------+---------+---------+---------+ 120
      CTACTATTTAGGTCACGTGGTAATCTACATCAACCATGAAACACATTTACCGGACTGAAG

D  D  K  S  S  A  P  L  D  V  V  G  T  L  C  K  W  P  D  F   -

TTAAAGATGAGTAAGGACATTTATGGTGACAGTTTATTCTTCTTTGGCCGAAGGGAACAG
121   ---------+---------+---------+---------+---------+---------+ 180
      AATTTCTACTCATTCCTGTAAATACCACTGTCAAATAAGAAGAAACCGGCTTCCCTTGTC

L  K  M  S  K  D  I  Y  G  D  S  L  F  F  F  G  R  R  E  Q   -

CTTTATGCAAGACACTTTTTTGTTAGAGCTGGGACAATGGGTGATGCGTTACCAGAGCCT
181   ---------+---------+---------+---------+---------+---------+ 240
      GAAATACGTTCTGTGAAAAAACAATCTCGACCCTGTTACCCACTACGCAATGGTCTCGGA

L  Y  A  R  H  F  F  V  R  A  G  T  M  G  D  A  L  P  E  P   -

TTTGAAGTGAAGTCTGATTACATAATTGCTGCTCAGAGTAACCAAGAACAAAATAATCTT
241   ---------+---------+---------+---------+---------+---------+ 300
      AAACTTCACTTCAGACTAATGTATTAACGACGAGTCTCATTGGTTCTTGTTTTATTAGAA

F  E  V  K  S  D  Y  I  I  A  A  Q  S  N  Q  E  Q  N  N  L   -

GGCCCTCACATTTATTTTGGAACTCCTAGCGGTTCTCTTGTATCAAGTGAATCTCAGCTT
301   ---------+---------+---------+---------+---------+---------+ 360
      CCGGGAGTGTAAATAAAACCTTGAGGATCGCCAAGAGAACATAGTTCACTTAGAGTCGAA

G  P  H  I  Y  F  G  T  P  S  G  S  L  V  S  S  E  S  Q  L   -

TTTAACCGACCGTATTGGTTAAACAGAGCTCAGGGCACTAATAACGGCAT
361   ---------+---------+---------+---------+---------+ 410
      AAATTGGCTGGCATAACCAATTTGTCTCGAGTCCCGTGATTATTGCCGTA

DL35.seq from 1 to 383:

```
     ATAGAGGATGGGGAAATGGTTGAAACTGGGTTCGGGGCCCTGGATTTTGCCGCTCTACAG
  1  ---------+---------+---------+---------+---------+---------+  60
     TATCTCCTACCCCTTTACCAACTTTGACCCAAGCCCCGGGACCTAAAACGGCGAGATGTC

I  E  D  G  E  M  V  E  T  G  F  G  A  L  D  F  A  A  L  Q   -

TCCAACAAATCTGATGTCCCCCTGGATATTTGTACTAACATATGTAAATATCCGGACTAT
 61  ---------+---------+---------+---------+---------+---------+ 120
     AGGTTGTTTAGACTACAGGGGGACCTATAAACATGATTGTATACATTTATAGGCCTGATA

S  N  K  S  D  V  P  L  D  I  C  T  N  I  C  K  Y  P  D  Y   -

CTGAAAATGGCTGCTGACCCCTATGGCGATTCTATGTTCTTTTCCCTGCGCAGGGAGCAG
121  ---------+---------+---------+---------+---------+---------+ 180
     GACTTTTACCGACGACTGGGGATACCGCTAAGATACAAGAAAAGGGACGCGTCCCTCGTC

L  K  M  A  A  D  P  Y  G  D  S  M  F  F  S  L  R  R  E  Q   -

ATGTTCACCCGGCATTTCTTCAATCGGGGTGGGTCGATGGGTGACGCCCTCCCGGAGGAG
181  ---------+---------+---------+---------+---------+---------+ 240
     TACAAGTGGGCCGTAAAGAAGTTAGCCCCACCCAGCTACCCACTGCGGGAGGGCCTCCTC

M  F  T  R  H  F  F  N  R  G  G  S  M  G  D  A  L  P  E  E   -

CTATACGTCAAAAGTTCTACCGTGCAGACCCCAGGTAGTTATGTTTACACCTCCACTCCC
241  ---------+---------+---------+---------+---------+---------+ 300
     GATATGCAGTTTTCAAGATGGCACGTCTGGGGTCCATCAATACAAATGTGGAGGTGAGGG

L  Y  V  K  S  S  T  V  Q  T  P  G  S  Y  V  Y  T  S  T  P   -

AGTGGCTCTATGGTATCCTCTGAACAGCAGTTATTTAACAAGCCTTACTGGCTGCGGAGG
301  ---------+---------+---------+---------+---------+---------+ 360
     TCACCGAGATACCATAGGAGACTTGTCGTCAATAAATTGTTCGGAATGACCGACGCCTCC

S  G  S  M  V  S  S  E  Q  Q  L  F  N  K  P  Y  W  L  R  R   -

GCTCAAGGTACTAATAACGGCGT
361  ---------+---------+--- 383
     CGAGTTCCATGATTATTGCCGCS

DL40.seq from 1 to 386:

```
    ATGGAAGACGGAGATATGGTAGACACTGGCTATGGTGCTATGGACTTCACTGCATTACAG
  1 ---------+---------+---------+---------+---------+---------+ 60
    TACCTTCTGCCTCTATACCATCTGTGACCGATACCACGATACCTGAAGTGACGTAATGTC

M  E  D  G  D  M  V  D  T  G  Y  G  A  M  D  F  T  A  L  Q   -

TTAAATAAGTCTGACGTGCCTATAGATATTTGCCAGTCCACTTGTAAATACCCTGATTAT
 61 ---------+---------+---------+---------+---------+---------+ 120
    AATTTATTCAGACTGCACGGATATCTATAAACGGTCAGGTGAACATTTATGGGACTAATA

L  N  K  S  D  V  P  I  D  I  C  Q  S  T  C  K  Y  P  D  Y   -

TTGGGCATGGCAGCAGAGCCTTATGGCGACAGCATGTTTTTTTATTTGCGCAGAGAGCAA
121 ---------+---------+---------+---------+---------+---------+ 180
    AACCCGTACCGTCGTCTCGGAATACCGCTGTCGTACAAAAAAATAAACGCGTCTCTCGTT

L  G  M  A  A  E  P  Y  G  D  S  M  F  F  Y  L  R  R  E  Q   -

CTGTTTGCAAGACATTTTTTCAATAGAGCCAGTGCAGTGGGAGACACCATTCCTGACACT
181 ---------+---------+---------+---------+---------+---------+ 240
    GACAAACGTTCTGTAAAAAAGTTATCTCGGTCACGTCACCCTCTGTGGTAAGGACTGTGA

L  F  A  R  H  F  F  N  R  A  S  A  V  G  D  T  I  P  D  T   -

TTAATATTGAAGTCGGCCAGTGGTGACCAAAACGTTGGTAGTGCTGTGTATAGCCCCACT
241 ---------+---------+---------+---------+---------+---------+ 300
    AATTATAACTTCAGCCGGTCACCACTGGTTTTGCAACCATCACGACACATATCGGGGTGA

L  I  L  K  S  A  S  G  D  Q  N  V  G  S  A  V  Y  S  P  T   -

CCCAGTGGGTCCATGGTAACATCTGAGGCTCAATTATTTAATAAGCCATATTGGCTGAAG
301 ---------+---------+---------+---------+---------+---------+ 360
    GGGTCACCCAGGTACCATTGTAGACTCCGAGTTAATAAATTATTCGGTATAACCGACTTC

P  S  G  S  M  V  T  S  E  A  Q  L  F  N  K  P  Y  W  L  K   -

CGGGCTCAAGGACATAACAATGGTGT
361 ---------+---------+------ 386
    GCCCGAGTTCCTGTATTGTTACCACA

DL78.seq from 1 to 386:

```
    CTGGAGGATGCGGAAATGGTAGACACTGGATATGGTGCCATGGACTTTACTGCATTACAG
  1 ---------+---------+---------+---------+---------+---------+ 60
    GACCTCCTACGCCTTTACCATCTGTGACCTATACCACGGTACCTGAAATGACGTAATGTC

L  E  D  A  E  M  V  D  T  G  Y  G  A  M  D  F  T  A  L  Q   -

TTAAATAAGTCTGACGTGCCTATCGATATTTGCCAGTCTACCTGTAAATATCCTGATTAT
 61 ---------+---------+---------+---------+---------+---------+ 120
    AATTTATTCAGACTGCACGGATAGCTATAAACGGTCAGATGGACATTTATAGGACTAATA

L  N  K  S  D  V  P  I  D  I  C  Q  S  T  C  K  Y  P  D  Y   -

TTGGGCATGGCAGCAGAGCCTTATGGCGACAGCATGTTTTTTTATTTGCGCAGGGAACAA
121 ---------+---------+---------+---------+---------+---------+ 180
    AACCCGTACCGTCGTCTCGGAATACCGCTGTCGTACAAAAAAATAAACGCGTCCCTTGTT

L  G  M  A  A  E  P  Y  G  D  S  M  F  F  Y  L  R  R  E  Q   -

CTGTTTGCCAGACATTTTTTTAATAGGGCTAGTGCAGTTGGGGACACCATTCCTGACACT
181 ---------+---------+---------+---------+---------+---------+ 240
    GACAAACGGTCTGTAAAAAAATTATCCCGATCACGTCAACCCCTGTGGTAAGGACTGTGA

L  F  A  R  H  F  F  N  R  A  S  A  V  G  D  T  I  P  D  T   -

TTGATATTGAAGGCAGCCAGTGGAGGGCAAAACGTTGGTAGTGCTGTTTACAGCCCCACA
241 ---------+---------+---------+---------+---------+---------+ 300
    AACTATAACTTCCGTCGGTCACCTCCCGTTTTGCAACCATCACGACAAATGTCGGGGTGT

L  I  L  K  A  A  S  G  G  Q  N  V  G  S  A  V  Y  S  P  T   -

CCCAGTGGGTCCATGGTAACATCTGAGGCTCAATTGTTTAATAAGCCATATTGGCTACGG
301 ---------+---------+---------+---------+---------+---------+ 360
    GGGTCACCCAGGTACCATTGTAGACTCCGAGTTAACAAATTATTCGGTATAACCGATGCC

P  S  G  S  M  V  T  S  E  A  Q  L  F  N  K  P  Y  W  L  R   -

CGGGCTCAAGGAACGAACAACGGAGT
361 ---------+---------+------ 386
    GCCCGAGTTCCTTGCTTGTTGCCTCA

DL82.seq from 1 to 413:

```
    ATCGAGGATGGGGATATGTGTGATATTGGTTTTGGAAACATGAATTTCAGTATATTACAA
1   ---------+---------+---------+---------+---------+---------+  60
    TAGCTCCTACCCCTATACACACTATAACCAAAACCTTTGTACTTAAAGTCATATAATGTT

I  E  D  G  D  M  C  D  I  G  F  G  N  M  N  F  S  I  L  Q    -

CAAGACAGATCAGGTGTTCCTTTGGATATAGTAGCTTCCATTTGCAAATGGCCAGATCTT
61  ---------+---------+---------+---------+---------+---------+  120
    GTTCTGTCTAGTCCACAAGGAAACCTATATCATCGAAGGTAAACGTTTACCGGTCTAGAA

Q  D  R  S  G  V  P  L  D  I  V  A  S  I  C  K  W  P  D  L    -

GGTAAAATGACCAATGATGTGTATGGTGATGAACTATTCTTTTTTGGTAAACGGGAGCAG
121 ---------+---------+---------+---------+---------+---------+  180
    CCATTTTACTGGTTACTACACATACCACTACTTGATAAGAAAAAACCATTTGCCCTCGTC

G  K  M  T  N  D  V  Y  G  D  E  L  F  F  F  G  K  R  E  Q    -

GTTTATGCAAGGCATTATTTTACAAGGCATGGTGTTGTAGGAGAAGATATTCCTCAGGTA
181 ---------+---------+---------+---------+---------+---------+  240
    CAAATACGTTCCGTAATAAAATGTTCCGTACCACAACATCCTCTTCTATAAGGAGTCCAT

V  Y  A  R  H  Y  F  T  R  H  G  V  V  G  E  D  I  P  Q  V    -

AATGAGGACCCTACAACTAAATACCTGCGAGGAGGTGAAGGTGGTCAAAATCAGGCTACT
241 ---------+---------+---------+---------+---------+---------+  300
    TTACTCCTGGGATGTTGATTTATGGACGCTCCTCCACTTCCACCAGTTTTAGTCCGATGA

N  E  D  P  T  T  K  Y  L  R  G  G  E  G  G  Q  N  Q  A  T    -

GTTTCATCCTCTGTATATTTTGCAACTCCCAGTGGTTCCTTGGTGTCCAGTGATGCTCAA
301 ---------+---------+---------+---------+---------+---------+  360
    CAAAGTAGGAGACATATAAAACGTTGAGGGTCACCAAGGAACCACAGGTCACTACGAGTT

V  S  S  S  V  Y  F  A  T  P  S  G  S  L  V  S  S  D  A  Q    -

ATTATGAACAGGCCTTATTGGGTACAACGCGCGCAGGGAACGAACAACGGCGT
361 ---------+---------+---------+---------+---------+---  413
    TAATACTTGTCCGGAATAACCCATGTTGCGCGCGTCCCTTGCTTGTTGCCGCA

DL83.seq from 1 to 395:

```
     CTGGAGGATGGCGACATGTGTGATGTAGGATTTGGAGCTGCAAATTTTAAAACACTTCAG
  1  ---------+---------+---------+---------+---------+---------+  60
     GACCTCCTACCGCTGTACACACTACATCCTAAACCTCGACGTTTAAAATTTTGTGAAGTC

L   E   D   G   D   M   C   D   V   G   F   G   A   A   N   F   K   T   L   Q   -

GAAGATAAATCAGGAGTACCTATGGATCTTTTAAATGAAACTTGTAAATATCCTGACTTT
 61  ---------+---------+---------+---------+---------+---------+ 120
     CTTCTATTTAGTCCTCATGGATACCTAGAAAATTTACTTTGAACATTTATAGGACTGAAA

E   D   K   S   G   V   P   M   D   L   L   N   E   T   C   K   Y   P   D   F   -

CTTCAGATGTCAAAAGACAAATATGGAGACAGTTTGTTCTTTTTTGGAAGAAAGGAACAA
121  ---------+---------+---------+---------+---------+---------+ 180
     GAAGTCTACAGTTTTCTGTTTATACCTCTGTCAAACAAGAAAAAACCTTCTTTCCTTGTT

L   Q   M   S   K   D   K   Y   G   D   S   L   F   F   F   G   R   K   E   Q   -

CTTTACGCGAGACACTTTTATGTTAGAGGAGGTGTTGATGGCGATGCATTGCCATTAACT
181  ---------+---------+---------+---------+---------+---------+ 240
     GAAATGCGCTCTGTGAAAATACAATCTCCTCCACAACTACCGCTACGTAACGGTAATTGA

L   Y   A   R   H   F   Y   V   R   G   G   V   D   G   D   A   L   P   L   T   -

AACTTTATTTATGGTGCTCAGCAGGACAAACCTCAAAACAATTTAGGACCATATACTTAC
241  ---------+---------+---------+---------+---------+---------+ 300
     TTGAAATAAATACCACGAGTCGTCCTGTTTGGAGTTTTGTTAAATCCTGGTATATGAATG

N   F   I   Y   G   A   Q   Q   D   K   P   Q   N   N   L   G   P   Y   T   Y   -

TTTCCTACTCCTAGTGGCTCTTTATACTCAACCGATAATCAATTATTTAACAGACCCTAT
301  ---------+---------+---------+---------+---------+---------+ 360
     AAAGGATGAGGATCACCGAGAAATATGAGTTGGCTATTAGTTAATAAATTGTCTGGGATA

F   P   T   P   S   G   S   L   Y   S   T   D   N   Q   L   F   N   R   P   Y   -

TGGCTTAGCCAGGCTCAGGGCACAAACAATGGGAT
361  ---------+---------+---------+----- 395
     ACCGAATCGGTCCGAGTCCCGTGTTTGTTACCCTA

DL84.seq from 1 to 407:

```
    CTAGAAGACGCGGAGATGAGTGATATTGGTTTGGGGGCAGTTAATTTTCATACGTTTTCG
  1 ---------+---------+---------+---------+---------+---------+ 60
    GATCTTCTGCGCCTCTACTCACTATAACCAAACCCCCGTCAATTAAAAGTATGCAAAAGC

L  E  D  A  E  M  S  D  I  G  L  G  A  V  N  F  H  T  F  S  -

GCCTCCCGTTCAGATGCTCCTTTAGAAGTTATAGATTCAATTTGCAAATGGCCTGATTTT
 61 ---------+---------+---------+---------+---------+---------+ 120
    CGGAGGGCAAGTCTACGAGGAAATCTTCAATATCTAAGTTAAACGTTTACCGGACTAAAA

A  S  R  S  D  A  P  L  E  V  I  D  S  I  C  K  W  P  D  F  -

GTTCAGATGACAAAAGATGTTTATGGAGATAAGATCTGGTTTTATGGAAAACGGGAACAG
121 ---------+---------+---------+---------+---------+---------+ 180
    CAAGTCTACTGTTTTCTACAAATACCTCTATTCTAGACCAAAATACCTTTTGCCCTTGTC

V  Q  M  T  K  D  V  Y  G  D  K  I  W  F  Y  G  K  R  E  Q  -

CTTTATGCCAGACATATGTTTGTTAAGGATGGTGTGGACGGTGACAGTATTCCAAATGAG
181 ---------+---------+---------+---------+---------+---------+ 240
    GAAATACGGTCTGTATACAAACAATTCCTACCACACCTGCCACTGTCATAAGGTTTACTC

L  Y  A  R  H  M  F  V  K  D  G  V  D  G  D  S  I  P  N  E  -

CCCACACACGCTTATTATATTCCCCCACCCACAGGTTCTGCCCAGGAAACTAATTTTGGA
241 ---------+---------+---------+---------+---------+---------+ 300
    GGGTGTGTGCGAATAATATAAGGGGGTGGGTGTCCAAGACGGGTCCTTTGATTAAAACCT

P  T  H  A  Y  Y  I  P  P  P  T  G  S  A  Q  E  T  N  F  G  -

AAGATAAGTTACTTTCCAGTTCCCAGTGGATCTTTGGTGTCCAGTGAGGCTACTATATTT
301 ---------+---------+---------+---------+---------+---------+ 360
    TTCTATTCAATGAAAGGTCAAGGGTCACCTAGAAACCACAGGTCACTCCGATGATATAAA

K  I  S  Y  F  P  V  P  S  G  S  L  V  S  S  E  A  T  I  F  -

AATAGACCTTATTGGTTGCACAAAGCTCAAGGAACAAACAATGGAAT
361 ---------+---------+---------+---------+------- 407
    TTATCTGGAATAACCAACGTGTTTCGAGTTCCTTGTTTGTTACCTTA

DL100.seq from 1 to 413:

```
    ATTGAGGACGGTGATATGATCGATATTGGGTTTGGCAATATAAATAACAAGACATTATCA
  1 ---------+---------+---------+---------+---------+---------+  60
    TAACTCCTGCCACTATACTAGCTATAACCCAAACCGTTATATTTATTGTTCTGTAATAGT

I  E  D  G  D  M  I  D  I  G  F  G  N  I  N  N  K  T  L  S  -

GTAAACAAATCAGATGTTAGTTTAGATTTAGTAAATGAAATAGCTAAATATCCAGATTTT
 61 ---------+---------+---------+---------+---------+---------+ 120
    CATTTGTTTAGTCTACAATCAAATCTAAATCATTTACTTTATCGATTTATAGGTCTAAAA

V  N  K  S  D  V  S  L  D  L  V  N  E  I  A  K  Y  P  D  F  -

TTAACAATGGCTAATGATGTGTATGGCGATTCTTGCTTTTTTTTTGCCAGGAGAGAACAA
121 ---------+---------+---------+---------+---------+---------+ 180
    AATTGTTACCGATTACTACACATACCGCTAAGAACGAAAAAAAAACGGTCCTCTCTTGTT

L  T  M  A  N  D  V  Y  G  D  S  C  F  F  F  A  R  R  E  Q  -

TGTTATGCTAGACATTATTTTACTAGAGGAGGAGCTGTGGGTGATGCTATACCTGATACA
181 ---------+---------+---------+---------+---------+---------+ 240
    ACAATACGATCTGTAATAAAATGATCTCCTCCTCGACACCCACTACGATATGGACTATGT

C  Y  A  R  H  Y  F  T  R  G  G  A  V  G  D  A  I  P  D  T  -

ACAACTAATCAAGATCACAAATACTATCTAGCACCTAAGAGTGGACAATCCCAAAGTCCT
241 ---------+---------+---------+---------+---------+---------+ 300
    TGTTGATTAGTTCTAGTGTTTATGATAGATCGTGGATTCTCACCTGTTAGGGTTTCAGGA

T  T  N  Q  D  H  K  Y  Y  L  A  P  K  S  G  Q  S  Q  S  P  -

TTGGGTAATTCTATTTACTATCCCACCGTTAGTGGCTCCTTAGTTTCTTCTGATGCACAG
301 ---------+---------+---------+---------+---------+---------+ 360
    AACCCATTAAGATAAATGATAGGGTGGCAATCACCGAGGAATCAAAGAAGACTACGTGTC

L  G  N  S  I  Y  Y  P  T  V  S  G  S  L  V  S  S  D  A  Q  -

CTCTTTAACAGACCCTTCTGGTTGAAACGTGCACAGGGGCACAATAACGGCAT
361 ---------+---------+---------+---------+---------+--- 413
    GAGAAATTGTCTGGGAAGACCAACTTTGCACGTGTCCCCGTGTTATTGCCGTA

HR22.seq from 1 to 404:

```
     ATACAGGATGGGGACATGTTTGATATAGGTTTTGGTAATATTAACAATAAAACTCTATCT
  1  ---------+---------+---------+---------+---------+---------+ 60
     TATGTCCTACCCCTGTACAAACTATATCCAAAACCATTATAATTGTTATTTTGAGATAGA

I  Q  D  G  D  M  F  D  I  G  F  G  N  I  N  N  K  T  L  S  -

TATAATAAGTCTGATGTAAGTTTAGACATTGTTAATGAAGTATGCAAATATCCAGATTTT
 61  ---------+---------+---------+---------+---------+---------+ 120
     ATATTATTCAGACTACATTCAAATCTGTAACAATTACTTCATACGTTTATAGGTCTAAAA

Y  N  K  S  D  V  S  L  D  I  V  N  E  V  C  K  Y  P  D  F  -

TTGACAATGTCTAATGATGTGTATGGAGACGCATGCTTTTACTGTGCCCGAAGAGAGCAA
121  ---------+---------+---------+---------+---------+---------+ 180
     AACTGTTACAGATTACTACACATACCTCTGCGTACGAAAATGACACGGGCTTCTCTCGTT

L  T  M  S  N  D  V  Y  G  D  A  C  F  Y  C  A  R  R  E  Q  -

TGTTATGCTAGACATTATTTTGTTCGGGGAGGTCAGGTTGGAGATGCAATACCTGACGAG
181  ---------+---------+---------+---------+---------+---------+ 240
     ACAATACGATCTGTAATAAAACAAGCCCCTCCAGTCCAACCTCTACGTTATGGACTGCTC

C  Y  A  R  H  Y  F  V  R  G  G  Q  V  G  D  A  I  P  D  E  -

GCAGTCCAACAAGATCACAAATATTATTTACCTTCTGATACACGGCGCACTTTAGAAAAC
241  ---------+---------+---------+---------+---------+---------+ 300
     CGTCAGGTTGTTCTAGTGTTTATAATAAATGGAAGACTATGTGCCGCGTGAAATCTTTTG

A  V  Q  Q  D  H  K  Y  Y  L  P  S  D  T  R  R  T  L  E  N  -

TCCACCTATTTTCCCACCGTAAGCGGGTCGTTGGTGACCTCTGATGCCCAACTATTTAAT
301  ---------+---------+---------+---------+---------+---------+ 360
     AGGTGGATAAAAGGGTGGCATTCGCCCAGCAACCACTGGAGACTACGGGTTGATAAATTA

S  T  Y  F  P  T  V  S  G  S  L  V  T  S  D  A  Q  L  F  N  -

AGGCCCTTTTGGTTAAAACGTGCACAAGGCCACAATAACGGAAT
361  ---------+---------+---------+---------+---- 404
     TCCGGGAAAACCAATTTTGCACGTGTTCCGGTGTTATTGCCTTA

R  P  F  W  L  K  R  A  Q  G  H  N  N  G      -
```

SEQUENCE LISTING

<160> NUMBER OF SEQ ID NOS: 33

<210> SEQ ID NO 1
<211> LENGTH: 416
<212> TYPE: DNA
<213> ORGANISM: Papilloma virus
<220> FEATURE:
<221> NAME/KEY: CDS
<222> LOCATION: (1)...(414)

<400> SEQUENCE: 1

```
ctc gag gat ggg gaa atg tgc gat att gga ttt gga gca tgc aat ttt      48
Leu Glu Asp Gly Glu Met Cys Asp Ile Gly Phe Gly Ala Cys Asn Phe
 1               5                  10                  15 aaa cag tta cag aag gat aga tct ggt gtt cca tta gat ata gta gag      96
Lys Gln Leu Gln Lys Asp Arg Ser Gly Val Pro Leu Asp Ile Val Glu
             20                  25                  30 agc act tgt aag tat cct gat ttt tta aag atg ggt aag gat atg tat     144
Ser Thr Cys Lys Tyr Pro Asp Phe Leu Lys Met Gly Lys Asp Met Tyr
         35                  40                  45 ggc gac gag cta ttt ttc tat ggc aga cga gaa cag tta tat gta aga     192
Gly Asp Glu Leu Phe Phe Tyr Gly Arg Arg Glu Gln Leu Tyr Val Arg
     50                  55                  60 cat aac ttt tct cgt gca ggc act gta gga gat agt ata cct tta cct     240
His Asn Phe Ser Arg Ala Gly Thr Val Gly Asp Ser Ile Pro Leu Pro
 65                  70                  75                  80 gat cag gat act gca ttt tat aga agt cct aat act gca aat aat gat     288
Asp Gln Asp Thr Ala Phe Tyr Arg Ser Pro Asn Thr Ala Asn Asn Asp
                 85                  90                  95 ttg cct caa aat aca tta gcg tct cac ata tac tgt gcc atc cca agt     336
Leu Pro Gln Asn Thr Leu Ala Ser His Ile Tyr Cys Ala Ile Pro Ser
            100                 105                 110 ggt tct tta acc agt agt gat tct caa tta ttt aat agg cct tat tgg     384
Gly Ser Leu Thr Ser Ser Asp Ser Gln Leu Phe Asn Arg Pro Tyr Trp
        115                 120                 125 ctg caa aat gct cag ggc acc aac aac ggc gt                          416
Leu Gln Asn Ala Gln Gly Thr Asn Asn Gly
    130                 135
```

<210> SEQ ID NO 2
<211> LENGTH: 138
<212> TYPE: PRT
<213> ORGANISM: Papilloma virus

<400> SEQUENCE: 2

```
Leu Glu Asp Gly Glu Met Cys Asp Ile Gly Phe Gly Ala Cys Asn Phe
 1               5                  10                  15

Lys Gln Leu Gln Lys Asp Arg Ser Gly Val Pro Leu Asp Ile Val Glu
             20                  25                  30

Ser Thr Cys Lys Tyr Pro Asp Phe Leu Lys Met Gly Lys Asp Met Tyr
         35                  40                  45

Gly Asp Glu Leu Phe Phe Tyr Gly Arg Arg Glu Gln Leu Tyr Val Arg
     50                  55                  60

His Asn Phe Ser Arg Ala Gly Thr Val Gly Asp Ser Ile Pro Leu Pro
 65                  70                  75                  80

Asp Gln Asp Thr Ala Phe Tyr Arg Ser Pro Asn Thr Ala Asn Asn Asp
                 85                  90                  95

Leu Pro Gln Asn Thr Leu Ala Ser His Ile Tyr Cys Ala Ile Pro Ser
            100                 105                 110
```

```
Gly Ser Leu Thr Ser Ser Asp Ser Gln Leu Phe Asn Arg Pro Tyr Trp
        115                 120                 125
Leu Gln Asn Ala Gln Gly Thr Asn Asn Gly
    130                 135

<210> SEQ ID NO 3
<211> LENGTH: 416
<212> TYPE: DNA
<213> ORGANISM: Papilloma virus

<400> SEQUENCE: 3
acgccgttgt tggtgccctg agcattttgc agccaataag gcctattaaa taattgagaa      60
tcactactgg ttaaagaacc acttgggatg cacagtata tgtgagacgc taatgtattt     120
tgaggcaaat cattatttgc agtattagga cttctataaa atgcagtatc ctgatcaggt     180
aaaggtatac tatctcctac agtgcctgca cgagaaaagt tatgtcttac ataractgt      240 tctcgtctgc catagaaaaa tagctcgtcg ccatacatat ccttacccat ctttaaaaaa     300
tcaggatact tacaagtgct ctctactata tctaatggaa caccagatct atccttctgt     360
aactgtttaa aattgcatgc tccaaatcca atatcgcaca tttccccatc ctcgag         416

<210> SEQ ID NO 4
<211> LENGTH: 386
<212> TYPE: DNA
<213> ORGANISM: Papilloma virus
<220> FEATURE:
<221> NAME/KEY: CDS
<222> LOCATION: (1)...(384)

<400> SEQUENCE: 4 att gag gat ggt gat atg gta gac ata gga ttt ggg aat tgt aat ttt       48
Ile Glu Asp Gly Asp Met Val Asp Ile Gly Phe Gly Asn Cys Asn Phe
 1               5                  10                  15 aaa gct tta caa cag gac aag gct ggt acg cct tta gag tta act aat       96
Lys Ala Leu Gln Gln Asp Lys Ala Gly Thr Pro Leu Glu Leu Thr Asn
            20                  25                  30 gaa aaa tgt aag tgg cca gat ttt ctg aag atg gaa aaa gac act tat      144
Glu Lys Cys Lys Trp Pro Asp Phe Leu Lys Met Glu Lys Asp Thr Tyr
        35                  40                  45 gga gac cag atg ttt ttc tgt ggc agg aag gag caa atg tat tct agg      192
Gly Asp Gln Met Phe Phe Cys Gly Arg Lys Glu Gln Met Tyr Ser Arg
    50                  55                  60 cat atg ctt gct aaa gcg ggt att gat ggt gat cat ata cca gaa tca      240
His Met Leu Ala Lys Ala Gly Ile Asp Gly Asp His Ile Pro Glu Ser
65                  70                  75                  80 tta tac cat tcg cca aag aat aat gga aat ggc att gct cct tac act      288
Leu Tyr His Ser Pro Lys Asn Asn Gly Asn Gly Ile Ala Pro Tyr Thr
                85                  90                  95 tac ttt cca acc aca agc ggt tcc tta gtc aca agt gat aat caa tta      336
Tyr Phe Pro Thr Thr Ser Gly Ser Leu Val Thr Ser Asp Asn Gln Leu
            100                 105                 110 ttt aac agg cca tat tgg ctt cat aat tca caa gga acc aat aac ggt      384
Phe Asn Arg Pro Tyr Trp Leu His Asn Ser Gln Gly Thr Asn Asn Gly
        115                 120                 125 at                                                                    386

<210> SEQ ID NO 5
<211> LENGTH: 128
<212> TYPE: PRT
<213> ORGANISM: Papilloma virus
```

<400> SEQUENCE: 5

```
Ile Glu Asp Gly Asp Met Val Asp Ile Gly Phe Gly Asn Cys Asn Phe
1               5                   10                  15

Lys Ala Leu Gln Gln Asp Lys Ala Gly Thr Pro Leu Glu Leu Thr Asn
                20                  25                  30

Glu Lys Cys Lys Trp Pro Asp Phe Leu Lys Met Glu Lys Asp Thr Tyr
            35                  40                  45

Gly Asp Gln Met Phe Phe Cys Gly Arg Lys Glu Gln Met Tyr Ser Arg
        50                  55                  60

His Met Leu Ala Lys Ala Gly Ile Asp Gly Asp His Ile Pro Glu Ser
65                  70                  75                  80

Leu Tyr His Ser Pro Lys Asn Asn Gly Asn Gly Ile Ala Pro Tyr Thr
                85                  90                  95

Tyr Phe Pro Thr Thr Ser Gly Ser Leu Val Thr Ser Asp Asn Gln Leu
            100                 105                 110

Phe Asn Arg Pro Tyr Trp Leu His Asn Ser Gln Gly Thr Asn Asn Gly
        115                 120                 125
```

<210> SEQ ID NO 6
<211> LENGTH: 386
<212> TYPE: DNA
<213> ORGANISM: Papilloma virus
<400> SEQUENCE: 6

```
ataccgttat tggttccttg tgaattatga agccaatatg gcctgttaaa taattgatta    60
tcacttgtga ctaaggaacc gcttgtggtt ggaaagtaag tgtaaggagc aatgccattt   120
ccattattct ttggcgaatg gtataatgat tctggtatat gatcaccatc aatacccgct   180
ttagcaagca tatgcctaga atacatttgc tccttcctgc cacagaaaaa catctggtct   240
ccataagtgt cttttccat cttcagaaaa tctggccact tacatttttc attagttaac    300
tctaaggcg taccagcctt gtcctgttgt aaagctttaa aattacaatt cccaaatcct    360
atgtctacca tatcaccatc ctcaat                                         386
```

<210> SEQ ID NO 7
<211> LENGTH: 410
<212> TYPE: DNA
<213> ORGANISM: Papilloma virus
<220> FEATURE:
<221> NAME/KEY: CDS
<222> LOCATION: (1)...(408)

<400> SEQUENCE: 7

```
ctg gag gat ggc gac atg tgt gat ata ggc ttt gga gct ttt aac ttt     48
Leu Glu Asp Gly Asp Met Cys Asp Ile Gly Phe Gly Ala Phe Asn Phe
1               5                   10                  15 aaa gct ttg cag gat gat aaa tcc agt gca cca tta gat gta gtt ggt     96
Lys Ala Leu Gln Asp Asp Lys Ser Ser Ala Pro Leu Asp Val Val Gly
                20                  25                  30 act ttg tgt aaa tgg cct gac ttc tta aag atg agt aag gac att tat    144
Thr Leu Cys Lys Trp Pro Asp Phe Leu Lys Met Ser Lys Asp Ile Tyr
            35                  40                  45 ggt gac agt tta ttc ttc ttt ggc cga agg gaa cag ctt tat gca aga    192
Gly Asp Ser Leu Phe Phe Phe Gly Arg Arg Glu Gln Leu Tyr Ala Arg
        50                  55                  60 cac ttt ttt gtt aga gct ggg aca atg ggt gat gcg tta cca gag cct    240
His Phe Phe Val Arg Ala Gly Thr Met Gly Asp Ala Leu Pro Glu Pro
65                  70                  75                  80
```

```
ttt gaa gtg aag tct gat tac ata att gct gct cag agt aac caa gaa      288
Phe Glu Val Lys Ser Asp Tyr Ile Ile Ala Ala Gln Ser Asn Gln Glu
             85                  90                  95 caa aat aat ctt ggc cct cac att tat ttt gga act cct agc ggt tct      336
Gln Asn Asn Leu Gly Pro His Ile Tyr Phe Gly Thr Pro Ser Gly Ser
            100                 105                 110 ctt gta tca agt gaa tct cag ctt ttt aac cga ccg tat tgg tta aac      384
Leu Val Ser Ser Glu Ser Gln Leu Phe Asn Arg Pro Tyr Trp Leu Asn
            115                 120                 125 aga gct cag ggc act aat aac ggc at                                   410
Arg Ala Gln Gly Thr Asn Asn Gly
    130                 135
```

<210> SEQ ID NO 8
<211> LENGTH: 136
<212> TYPE: PRT
<213> ORGANISM: Papilloma virus

<400> SEQUENCE: 8

```
Leu Glu Asp Gly Asp Met Cys Asp Ile Gly Phe Gly Ala Phe Asn Phe
 1               5                  10                  15

Lys Ala Leu Gln Asp Asp Lys Ser Ser Ala Pro Leu Asp Val Val Gly
            20                  25                  30

Thr Leu Cys Lys Trp Pro Asp Phe Leu Lys Met Ser Lys Asp Ile Tyr
        35                  40                  45

Gly Asp Ser Leu Phe Phe Phe Gly Arg Arg Glu Gln Leu Tyr Ala Arg
    50                  55                  60

His Phe Phe Val Arg Ala Gly Thr Met Gly Asp Ala Leu Pro Glu Pro
65                  70                  75                  80

Phe Glu Val Lys Ser Asp Tyr Ile Ile Ala Ala Gln Ser Asn Gln Glu
            85                  90                  95

Gln Asn Asn Leu Gly Pro His Ile Tyr Phe Gly Thr Pro Ser Gly Ser
            100                 105                 110

Leu Val Ser Ser Glu Ser Gln Leu Phe Asn Arg Pro Tyr Trp Leu Asn
            115                 120                 125

Arg Ala Gln Gly Thr Asn Asn Gly
    130                 135
```

<210> SEQ ID NO 9
<211> LENGTH: 410
<212> TYPE: DNA
<213> ORGANISM: Papilloma virus

<400> SEQUENCE: 9

```
atgccgttat tagtgccctg agctctgttt aaccaatacg gtcggttaaa aagctgagat      60
tcacttgata caagagaacc gctaggagtt ccaaaataaa tgtgagggcc aagattattt     120
tgttcttggt tactctgagc agcaattatg taatcagact tcacttcaaa aggctctggt     180
aacgcatcac ccattgtccc agctctaaca aaaaagtgtc ttgcataaag ctgttcccct     240
cggccaaaga agaataaact gtcaccataa atgtccttac tcatctttaa gaagtcaggc     300
catttacaca agtaccaac tacatctaat ggtgcactgg atttatcatc ctgcaaagct     360
ttaaagttaa aagctccaaa gcctatatca cacatgtcgc catcctccag               410
```

<210> SEQ ID NO 10
<211> LENGTH: 383
<212> TYPE: DNA
<213> ORGANISM: Papilloma virus

```
<220> FEATURE:
<221> NAME/KEY: CDS
<222> LOCATION: (1)...(381)

<400> SEQUENCE: 10 ata gag gat ggg gaa atg gtt gaa act ggg ttc ggg gcc ctg gat ttt      48
Ile Glu Asp Gly Glu Met Val Glu Thr Gly Phe Gly Ala Leu Asp Phe
 1               5                  10                  15 gcc gct cta cag tcc aac aaa tct gat gtc ccc ctg gat att tgt act      96
Ala Ala Leu Gln Ser Asn Lys Ser Asp Val Pro Leu Asp Ile Cys Thr
             20                  25                  30 aac ata tgt aaa tat ccg gac tat ctg aaa atg gct gct gac ccc tat     144
Asn Ile Cys Lys Tyr Pro Asp Tyr Leu Lys Met Ala Ala Asp Pro Tyr
         35                  40                  45 ggc gat tct atg ttc ttt tcc ctg cgc agg gag cag atg ttc acc cgg     192
Gly Asp Ser Met Phe Phe Ser Leu Arg Arg Glu Gln Met Phe Thr Arg
     50                  55                  60 cat ttc ttc aat cgg ggt ggg tcg atg ggt gac gcc ctc ccg gag gag     240
His Phe Phe Asn Arg Gly Gly Ser Met Gly Asp Ala Leu Pro Glu Glu
 65                  70                  75                  80 cta tac gtc aaa agt tct acc gtg cag acc cca ggt agt tat gtt tac     288
Leu Tyr Val Lys Ser Ser Thr Val Gln Thr Pro Gly Ser Tyr Val Tyr
                 85                  90                  95 acc tcc act ccc agt ggc tct atg gta tcc tct gaa cag cag tta ttt     336
Thr Ser Thr Pro Ser Gly Ser Met Val Ser Ser Glu Gln Gln Leu Phe
            100                 105                 110 aac aag cct tac tgg ctg cgg agg gct caa ggt act aat aac ggc         381
Asn Lys Pro Tyr Trp Leu Arg Arg Ala Gln Gly Thr Asn Asn Gly
        115                 120                 125 gt                                                                  383

<210> SEQ ID NO 11
<211> LENGTH: 127
<212> TYPE: PRT
<213> ORGANISM: Papilloma virus

<400> SEQUENCE: 11

Ile Glu Asp Gly Glu Met Val Glu Thr Gly Phe Gly Ala Leu Asp Phe
 1               5                  10                  15

Ala Ala Leu Gln Ser Asn Lys Ser Asp Val Pro Leu Asp Ile Cys Thr
             20                  25                  30

Asn Ile Cys Lys Tyr Pro Asp Tyr Leu Lys Met Ala Ala Asp Pro Tyr
         35                  40                  45

Gly Asp Ser Met Phe Phe Ser Leu Arg Arg Glu Gln Met Phe Thr Arg
     50                  55                  60

His Phe Phe Asn Arg Gly Gly Ser Met Gly Asp Ala Leu Pro Glu Glu
 65                  70                  75                  80

Leu Tyr Val Lys Ser Ser Thr Val Gln Thr Pro Gly Ser Tyr Val Tyr
                 85                  90                  95

Thr Ser Thr Pro Ser Gly Ser Met Val Ser Ser Glu Gln Gln Leu Phe
            100                 105                 110

Asn Lys Pro Tyr Trp Leu Arg Arg Ala Gln Gly Thr Asn Asn Gly
        115                 120                 125

<210> SEQ ID NO 12
<211> LENGTH: 383
<212> TYPE: DNA
<213> ORGANISM: Papilloma virus

<400> SEQUENCE: 12
```

-continued

```
acgccgttat tagtaccttg agccctccgc agccagtaag gcttgttaaa taactgctgt      60
tcagaggata ccatagagcc actgggagtg gaggtgtaaa cataactacc tgggtctgc       120 acggtagaac ttttgacgta tagctcctcc gggagggcgt cacccatcga cccaccccga     180
ttgaagaaat gccgggtgaa catctgctcc ctgcgcaggg aaaagaacat agaatcgcca     240 tagggggtcag cagccatttt cagatagtcc ggatatttac atatgttagt acaaatatcc    300 aggggggacat cagatttgtt ggactgtaga gcggcaaaat ccagggcccc gaacccagtt    360
tcaaccattt ccccatcctc tat                                             383
```

<210> SEQ ID NO 13
<211> LENGTH: 386
<212> TYPE: DNA
<213> ORGANISM: Papilloma virus
<220> FEATURE:
<221> NAME/KEY: CDS
<222> LOCATION: (1)...(384)

<400> SEQUENCE: 13

```
atg gaa gac gga gat atg gta gac act ggc tat ggt gct atg gac ttc     48
Met Glu Asp Gly Asp Met Val Asp Thr Gly Tyr Gly Ala Met Asp Phe
 1               5                  10                  15 act gca tta cag tta aat aag tct gac gtg cct ata gat att tgc cag     96
Thr Ala Leu Gln Leu Asn Lys Ser Asp Val Pro Ile Asp Ile Cys Gln
            20                  25                  30 tcc act tgt aaa tac cct gat tat ttg ggc atg gca gca gag cct tat    144
Ser Thr Cys Lys Tyr Pro Asp Tyr Leu Gly Met Ala Ala Glu Pro Tyr
        35                  40                  45 ggc gac agc atg ttt ttt tat ttg cgc aga gag caa ctg ttt gca aga    192
Gly Asp Ser Met Phe Phe Tyr Leu Arg Arg Glu Gln Leu Phe Ala Arg
 50                  55                  60 cat ttt ttc aat aga gcc agt gca gtg gga gac acc att cct gac act    240
His Phe Phe Asn Arg Ala Ser Ala Val Gly Asp Thr Ile Pro Asp Thr
 65                  70                  75                  80 tta ata ttg aag tcg gcc agt ggt gac caa aac gtt ggt agt gct gtg    288
Leu Ile Leu Lys Ser Ala Ser Gly Asp Gln Asn Val Gly Ser Ala Val
                85                  90                  95 tat agc ccc act ccc agt ggg tcc atg gta aca tct gag gct caa tta    336
Tyr Ser Pro Thr Pro Ser Gly Ser Met Val Thr Ser Glu Ala Gln Leu
            100                 105                 110 ttt aat aag cca tat tgg ctg aag cgg gct caa gga cat aac aat ggt    384
Phe Asn Lys Pro Tyr Trp Leu Lys Arg Ala Gln Gly His Asn Asn Gly
            115                 120                 125 gt                                                                   386
```

<210> SEQ ID NO 14
<211> LENGTH: 128
<212> TYPE: PRT
<213> ORGANISM: Papilloma virus

<400> SEQUENCE: 14

```
Met Glu Asp Gly Asp Met Val Asp Thr Gly Tyr Gly Ala Met Asp Phe
 1               5                  10                  15

Thr Ala Leu Gln Leu Asn Lys Ser Asp Val Pro Ile Asp Ile Cys Gln
            20                  25                  30

Ser Thr Cys Lys Tyr Pro Asp Tyr Leu Gly Met Ala Ala Glu Pro Tyr
        35                  40                  45

Gly Asp Ser Met Phe Phe Tyr Leu Arg Arg Glu Gln Leu Phe Ala Arg
 50                  55                  60
```

His Phe Phe Asn Arg Ala Ser Ala Val Gly Asp Thr Ile Pro Asp Thr
65                  70                  75                  80

Leu Ile Leu Lys Ser Ala Ser Gly Asp Gln Asn Val Gly Ser Ala Val
                85                  90                  95

Tyr Ser Pro Thr Pro Ser Gly Ser Met Val Thr Ser Glu Ala Gln Leu
                100                 105                 110

Phe Asn Lys Pro Tyr Trp Leu Lys Arg Ala Gln Gly His Asn Asn Gly
                115                 120                 125

<210> SEQ ID NO 15
<211> LENGTH: 386
<212> TYPE: DNA
<213> ORGANISM: Papilloma virus

<400> SEQUENCE: 15
acaccattgt tatgtccttg agcccgcttc agccaatatg gcttattaaa taattgagcc      60
tcagatgtta ccatggaccc actgggagtg gggctataca cagcactacc aacgttttgg    120
tcaccactgg ccgacttcaa tattaaagtg tcaggaatgg tgtctcccac tgcactggct    180
ctattgaaaa aatgtcttgc aaacagttgc tctctgcgca ataaaaaaa catgctgtcg     240 ccataaggct ctgctgccat gcccaaataa tcagggtatt tacaagtgga ctggcaaata    300
tctataggca cgtcagactt atttaactgt aatgcagtga agtccatagc accatagcca    360
gtgtctacca tatctccgtc ttccat                                        386

<210> SEQ ID NO 16
<211> LENGTH: 386
<212> TYPE: DNA
<213> ORGANISM: Papilloma virus
<220> FEATURE:
<221> NAME/KEY: CDS
<222> LOCATION: (1)...(384)

<400> SEQUENCE: 16 ctg gag gat gcg gaa atg gta gac act gga tat ggt gcc atg gac ttt      48
Leu Glu Asp Ala Glu Met Val Asp Thr Gly Tyr Gly Ala Met Asp Phe
1               5                   10                  15 act gca tta cag tta aat aag tct gac gtg cct atc gat att tgc cag      96
Thr Ala Leu Gln Leu Asn Lys Ser Asp Val Pro Ile Asp Ile Cys Gln
            20                  25                  30 tct acc tgt aaa tat cct gat tat ttg ggc atg gca gca gag cct tat    144
Ser Thr Cys Lys Tyr Pro Asp Tyr Leu Gly Met Ala Ala Glu Pro Tyr
        35                  40                  45 ggc gac agc atg ttt ttt tat ttg cgc agg gaa caa ctg ttt gcc aga    192
Gly Asp Ser Met Phe Phe Tyr Leu Arg Arg Glu Gln Leu Phe Ala Arg
    50                  55                  60 cat ttt ttt aat agg gct agt gca gtt ggg gac acc att cct gac act    240
His Phe Phe Asn Arg Ala Ser Ala Val Gly Asp Thr Ile Pro Asp Thr
65                  70                  75                  80 ttg ata ttg aag gca gcc agt gga ggg caa aac gtt ggt agt gct gtt    288
Leu Ile Leu Lys Ala Ala Ser Gly Gly Gln Asn Val Gly Ser Ala Val
                85                  90                  95 tac agc ccc aca ccc agt ggg tcc atg gta aca tct gag gct caa ttg    336
Tyr Ser Pro Thr Pro Ser Gly Ser Met Val Thr Ser Glu Ala Gln Leu
                100                 105                 110 ttt aat aag cca tat tgg cta cgg cgg gct caa gga acg aac aac gga    384
Phe Asn Lys Pro Tyr Trp Leu Arg Arg Ala Gln Gly Thr Asn Asn Gly
                115                 120                 125 gt                                                                 386

<210> SEQ ID NO 17
<211> LENGTH: 128
<212> TYPE: PRT
<213> ORGANISM: Papilloma virus

<400> SEQUENCE: 17

Leu Glu Asp Ala Glu Met Val Asp Thr Gly Tyr Gly Ala Met Asp Phe
1               5                   10                  15

Thr Ala Leu Gln Leu Asn Lys Ser Asp Val Pro Ile Asp Ile Cys Gln
            20                  25                  30

Ser Thr Cys Lys Tyr Pro Asp Tyr Leu Gly Met Ala Ala Glu Pro Tyr
        35                  40                  45

Gly Asp Ser Met Phe Phe Tyr Leu Arg Arg Glu Gln Leu Phe Ala Arg
    50                  55                  60

His Phe Phe Asn Arg Ala Ser Ala Val Gly Asp Thr Ile Pro Asp Thr
65                  70                  75                  80

Leu Ile Leu Lys Ala Ala Ser Gly Gly Gln Asn Val Gly Ser Ala Val
                85                  90                  95

Tyr Ser Pro Thr Pro Ser Gly Ser Met Val Thr Ser Glu Ala Gln Leu
            100                 105                 110

Phe Asn Lys Pro Tyr Trp Leu Arg Arg Ala Gln Gly Thr Asn Asn Gly
        115                 120                 125

<210> SEQ ID NO 18
<211> LENGTH: 386
<212> TYPE: DNA
<213> ORGANISM: Papilloma virus

<400> SEQUENCE: 18
actccgttgt tcgttccttg agcccgccgt agccaatatg gcttattaaa caattgagcc     60
tcagatgtta ccatggaccc actgggtgtg ggctgtaaa cagcactacc aacgttttgc    120
cctccactgg ctgccttcaa tatcaaagtg tcaggaatgg tgtccccaac tgcactagcc    180
ctattaaaaa aatgtctggc aaacagttgt tccctgcgca ataaaaaaa catgctgtcg    240 ccataaggct ctgctgccat gcccaaataa tcaggatatt tacaggtaga ctggcaaata    300
tcgataggca cgtcagactt atttaactgt aatgcagtaa agtccatggc accatatcca    360
gtgtctacca tttccgcatc ctccag                                          386

<210> SEQ ID NO 19
<211> LENGTH: 413
<212> TYPE: DNA
<213> ORGANISM: Papilloma virus
<220> FEATURE:
<221> NAME/KEY: CDS
<222> LOCATION: (1)...(411)

<400> SEQUENCE: 19 atc gag gat ggg gat atg tgt gat att ggt ttt gga aac atg aat ttc       48
Ile Glu Asp Gly Asp Met Cys Asp Ile Gly Phe Gly Asn Met Asn Phe
1               5                   10                  15 agt ata tta caa caa gac aga tca ggt gtt cct ttg gat ata gta gct       96
Ser Ile Leu Gln Gln Asp Arg Ser Gly Val Pro Leu Asp Ile Val Ala
            20                  25                  30 tcc att tgc aaa tgg cca gat ctt ggt aaa atg acc aat gat gtg tat      144
Ser Ile Cys Lys Trp Pro Asp Leu Gly Lys Met Thr Asn Asp Val Tyr
        35                  40                  45 ggt gat gaa cta ttc ttt ttt ggt aaa cgg gag cag gtt tat gca agg      192

```
                                                                  -continued Gly Asp Glu Leu Phe Phe Phe Gly Lys Arg Glu Gln Val Tyr Ala Arg
 50                  55                  60 cat tat ttt aca agg cat ggt gtt gta gga gaa gat att cct cag gta    240
His Tyr Phe Thr Arg His Gly Val Val Gly Glu Asp Ile Pro Gln Val
 65                  70                  75                  80 aat gag gac cct aca act aaa tac ctg cga gga ggt gaa ggt ggt caa    288
Asn Glu Asp Pro Thr Thr Lys Tyr Leu Arg Gly Gly Glu Gly Gly Gln
                 85                  90                  95 aat cag gct act gtt tca tcc tct gta tat ttt gca act ccc agt ggt    336
Asn Gln Ala Thr Val Ser Ser Ser Val Tyr Phe Ala Thr Pro Ser Gly
            100                 105                 110 tcc ttg gtg tcc agt gat gct caa att atg aac agg cct tat tgg gta    384
Ser Leu Val Ser Ser Asp Ala Gln Ile Met Asn Arg Pro Tyr Trp Val
        115                 120                 125 caa cgc gcg cag gga acg aac aac ggc gt                             413
Gln Arg Ala Gln Gly Thr Asn Asn Gly
    130                 135

<210> SEQ ID NO 20
<211> LENGTH: 137
<212> TYPE: PRT
<213> ORGANISM: Papilloma virus

<400> SEQUENCE: 20

Ile Glu Asp Gly Asp Met Cys Asp Ile Gly Phe Gly Asn Met Asn Phe
 1               5                  10                  15

Ser Ile Leu Gln Gln Asp Arg Ser Gly Val Pro Leu Asp Ile Val Ala
                20                  25                  30

Ser Ile Cys Lys Trp Pro Asp Leu Gly Lys Met Thr Asn Asp Val Tyr
            35                  40                  45

Gly Asp Glu Leu Phe Phe Phe Gly Lys Arg Glu Gln Val Tyr Ala Arg
 50                  55                  60

His Tyr Phe Thr Arg His Gly Val Val Gly Glu Asp Ile Pro Gln Val
 65                  70                  75                  80

Asn Glu Asp Pro Thr Thr Lys Tyr Leu Arg Gly Gly Glu Gly Gly Gln
                 85                  90                  95

Asn Gln Ala Thr Val Ser Ser Ser Val Tyr Phe Ala Thr Pro Ser Gly
            100                 105                 110

Ser Leu Val Ser Ser Asp Ala Gln Ile Met Asn Arg Pro Tyr Trp Val
        115                 120                 125

Gln Arg Ala Gln Gly Thr Asn Asn Gly
    130                 135

<210> SEQ ID NO 21
<211> LENGTH: 413
<212> TYPE: DNA
<213> ORGANISM: Papilloma virus

<400> SEQUENCE: 21
acgccgttgt cgttccctg cgcgcgttgt acccaataag gcctgttcat aatttgagca     60
tcactggaca ccaaggaacc actgggagtt gcaaaatata cagaggatga acagtagcc    120 tgattttgac caccttcacc tcctcgcagg tatttagttg tagggtcctc atttacctga   180
ggaatatctt ctcctacaac accatgcctt gtaaataat gccttgcata aacctgctcc    240
cgtttaccaa aaagaatag ttcatcacca tacacatcat tggtcatttt accaagatct     300
ggccatttgc aaatggaagc tactatatcc aaaggaacac ctgatctgtc ttgttgtaat   360
atactgaaat tcatgtttcc aaaaccaata tcacacatat ccccatcctc gat          413
```

<210> SEQ ID NO 22
<211> LENGTH: 395
<212> TYPE: DNA
<213> ORGANISM: Papilloma virus
<220> FEATURE:
<221> NAME/KEY: CDS
<222> LOCATION: (1)...(393)

<400> SEQUENCE: 22

| | | | | | | | | | | | | | | | | |
|---|---|---|---|---|---|---|---|---|---|---|---|---|---|---|---|---|
| ctg | gag | gat | ggc | gac | atg | tgt | gat | gta | gga | ttt | gga | gct | gca | aat | ttt | 48 |
| Leu | Glu | Asp | Gly | Asp | Met | Cys | Asp | Val | Gly | Phe | Gly | Ala | Ala | Asn | Phe | |
| 1 | | | | 5 | | | | | 10 | | | | | 15 | | |
| aaa | aca | ctt | cag | gaa | gat | aaa | tca | gga | gta | cct | atg | gat | ctt | tta | aat | 96 |
| Lys | Thr | Leu | Gln | Glu | Asp | Lys | Ser | Gly | Val | Pro | Met | Asp | Leu | Leu | Asn | |
| | | | 20 | | | | | 25 | | | | | 30 | | | |
| gaa | act | tgt | aaa | tat | cct | gac | ttt | ctt | cag | atg | tca | aaa | gac | aaa | tat | 144 |
| Glu | Thr | Cys | Lys | Tyr | Pro | Asp | Phe | Leu | Gln | Met | Ser | Lys | Asp | Lys | Tyr | |
| | | 35 | | | | | 40 | | | | | 45 | | | | |
| gga | gac | agt | ttg | ttc | ttt | ttt | gga | aga | aag | gaa | caa | ctt | tac | gcg | aga | 192 |
| Gly | Asp | Ser | Leu | Phe | Phe | Phe | Gly | Arg | Lys | Glu | Gln | Leu | Tyr | Ala | Arg | |
| 50 | | | | | 55 | | | | | 60 | | | | | | |
| cac | ttt | tat | gtt | aga | gga | ggt | gtt | gat | ggc | gat | gca | ttg | cca | tta | act | 240 |
| His | Phe | Tyr | Val | Arg | Gly | Gly | Val | Asp | Gly | Asp | Ala | Leu | Pro | Leu | Thr | |
| 65 | | | | | 70 | | | | | 75 | | | | | 80 | |
| aac | ttt | att | tat | ggt | gct | cag | cag | gac | aaa | cct | caa | aac | aat | tta | gga | 288 |
| Asn | Phe | Ile | Tyr | Gly | Ala | Gln | Gln | Asp | Lys | Pro | Gln | Asn | Asn | Leu | Gly | |
| | | | | 85 | | | | | 90 | | | | | 95 | | |
| cca | tat | act | tac | ttt | cct | act | cct | agt | ggc | tct | tta | tac | tca | acc | gat | 336 |
| Pro | Tyr | Thr | Tyr | Phe | Pro | Thr | Pro | Ser | Gly | Ser | Leu | Tyr | Ser | Thr | Asp | |
| | | | 100 | | | | | 105 | | | | | 110 | | | |
| aat | caa | tta | ttt | aac | aga | ccc | tat | tgg | ctt | agc | cag | gct | cag | ggc | aca | 384 |
| Asn | Gln | Leu | Phe | Asn | Arg | Pro | Tyr | Trp | Leu | Ser | Gln | Ala | Gln | Gly | Thr | |
| | | 115 | | | | | 120 | | | | | 125 | | | | |
| aac | aat | ggg | at | | | | | | | | | | | | | 395 |
| Asn | Asn | Gly | | | | | | | | | | | | | | |
| | | 130 | | | | | | | | | | | | | | |

<210> SEQ ID NO 23
<211> LENGTH: 131
<212> TYPE: PRT
<213> ORGANISM: Papilloma virus

<400> SEQUENCE: 23

Leu Glu Asp Gly Asp Met Cys Asp Val Gly Phe Gly Ala Ala Asn Phe
1               5                   10                  15

Lys Thr Leu Gln Glu Asp Lys Ser Gly Val Pro Met Asp Leu Leu Asn
            20                  25                  30

Glu Thr Cys Lys Tyr Pro Asp Phe Leu Gln Met Ser Lys Asp Lys Tyr
        35                  40                  45

Gly Asp Ser Leu Phe Phe Phe Gly Arg Lys Glu Gln Leu Tyr Ala Arg
    50                  55                  60

His Phe Tyr Val Arg Gly Val Asp Gly Asp Ala Leu Pro Leu Thr
65                  70                  75                  80

Asn Phe Ile Tyr Gly Ala Gln Gln Asp Lys Pro Gln Asn Asn Leu Gly
                85                  90                  95

Pro Tyr Thr Tyr Phe Pro Thr Pro Ser Gly Ser Leu Tyr Ser Thr Asp
            100                 105                 110

Asn Gln Leu Phe Asn Arg Pro Tyr Trp Leu Ser Gln Ala Gln Gly Thr
        115                 120                 125

Asn Asn Gly
    130

<210> SEQ ID NO 24
<211> LENGTH: 395
<212> TYPE: DNA
<213> ORGANISM: Papilloma virus

<400> SEQUENCE: 24

```
atcccattgt tgtgccctg agcctggcta agccaatagg gtctgttaaa taattgatta      60
tcggttgagt ataaagagcc actaggagta ggaaagtaag tatatggtcc taaattgttt     120
tgaggtttgt cctgctgagc accataaata aagttagtta atggcaatgc atcgccatca    180
acacctcctc taacataaaa gtgtctcgcg taaagttgtt cctttcttcc aaaaaagaac    240
aaactgtctc catatttgtc ttttgacatc tgaagaaagt caggatattt acaagtttca    300
tttaaaagat ccataggtac tcctgattta tcttcctgaa gtgttttaaa atttgcagct    360
ccaaatccta catcacacat gtcgccatcc tccag                                395
```

<210> SEQ ID NO 25
<211> LENGTH: 407
<212> TYPE: DNA
<213> ORGANISM: Papilloma virus
<220> FEATURE:
<221> NAME/KEY: CDS
<222> LOCATION: (1)...(405)

<400> SEQUENCE: 25

```
cta gaa gac gcg gag atg agt gat att ggt ttg ggg gca gtt aat ttt      48
Leu Glu Asp Ala Glu Met Ser Asp Ile Gly Leu Gly Ala Val Asn Phe
 1               5                  10                  15 cat acg ttt tcg gcc tcc cgt tca gat gct cct tta gaa gtt ata gat      96
His Thr Phe Ser Ala Ser Arg Ser Asp Ala Pro Leu Glu Val Ile Asp
             20                  25                  30 tca att tgc aaa tgg cct gat ttt gtt cag atg aca aaa gat gtt tat    144
Ser Ile Cys Lys Trp Pro Asp Phe Val Gln Met Thr Lys Asp Val Tyr
         35                  40                  45 gga gat aag atc tgg ttt tat gga aaa cgg gaa cag ctt tat gcc aga    192
Gly Asp Lys Ile Trp Phe Tyr Gly Lys Arg Glu Gln Leu Tyr Ala Arg
     50                  55                  60 cat atg ttt gtt aag gat ggt gtg gac ggt gac agt att cca aat gag    240
His Met Phe Val Lys Asp Gly Val Asp Gly Asp Ser Ile Pro Asn Glu
 65                  70                  75                  80 ccc aca cac gct tat tat att ccc cca ccc aca ggt tct gcc cag gaa    288
Pro Thr His Ala Tyr Tyr Ile Pro Pro Pro Thr Gly Ser Ala Gln Glu
                 85                  90                  95 act aat ttt gga aag ata agt tac ttt cca gtt ccc agt gga tct ttg    336
Thr Asn Phe Gly Lys Ile Ser Tyr Phe Pro Val Pro Ser Gly Ser Leu
            100                 105                 110 gtg tcc agt gag gct act ata ttt aat aga cct tat tgg ttg cac aaa    384
Val Ser Ser Glu Ala Thr Ile Phe Asn Arg Pro Tyr Trp Leu His Lys
        115                 120                 125 gct caa gga aca aac aat gga at                                      407
Ala Gln Gly Thr Asn Asn Gly
    130                 135
```

<210> SEQ ID NO 26
<211> LENGTH: 135
<212> TYPE: PRT
<213> ORGANISM: Papilloma virus -continued

```
<400> SEQUENCE: 26

Leu Glu Asp Ala Glu Met Ser Asp Ile Gly Leu Gly Ala Val Asn Phe
 1               5                  10                  15

His Thr Phe Ser Ala Ser Arg Ser Asp Ala Pro Leu Glu Val Ile Asp
             20                  25                  30

Ser Ile Cys Lys Trp Pro Asp Phe Val Gln Met Thr Lys Asp Val Tyr
         35                  40                  45

Gly Asp Lys Ile Trp Phe Tyr Gly Lys Arg Glu Gln Leu Tyr Ala Arg
     50                  55                  60

His Met Phe Val Lys Asp Gly Val Asp Gly Asp Ser Ile Pro Asn Glu
 65                  70                  75                  80

Pro Thr His Ala Tyr Tyr Ile Pro Pro Thr Gly Ser Ala Gln Glu
                 85                  90                  95

Thr Asn Phe Gly Lys Ile Ser Tyr Phe Pro Val Pro Ser Gly Ser Leu
                100                 105                 110

Val Ser Ser Glu Ala Thr Ile Phe Asn Arg Pro Tyr Trp Leu His Lys
            115                 120                 125

Ala Gln Gly Thr Asn Asn Gly
            130             135

<210> SEQ ID NO 27
<211> LENGTH: 407
<212> TYPE: DNA
<213> ORGANISM: Papilloma virus

<400> SEQUENCE: 27
attccattgt tgttccttg agctttgtgc aaccaataag gtctattaaa tatagtagcc      60
tcactggaca ccaaagatcc actgggaact ggaaagtaac ttatctttcc aaaattagtt   120
tcctgggcag aacctgtggg tgggggaata taataagcgt gtgtgggctc atttggaata   180
ctgtcaccgt ccacaccatc cttaacaaac atatgtctgg cataaagctg ttcccgtttt   240
ccataaaacc agatcttatc tccataaaca tcttttgtca tctgaacaaa atcaggccat   300
ttgcaaattg aatctataac ttctaaagga gcatctgaac gggaggccga aaacgtatga   360
aaattaactg cccccaaacc aatatcactc atctccgcgt cttctag                 407

<210> SEQ ID NO 28
<211> LENGTH: 413
<212> TYPE: DNA
<213> ORGANISM: Papilloma virus
<220> FEATURE:
<221> NAME/KEY: CDS
<222> LOCATION: (1)...(411)

<400> SEQUENCE: 28 att gag gac ggt gat atg atc gat att ggg ttt ggc aat ata aat aac     48
Ile Glu Asp Gly Asp Met Ile Asp Ile Gly Phe Gly Asn Ile Asn Asn
 1               5                  10                  15 aag aca tta tca gta aac aaa tca gat gtt agt tta gat tta gta aat    96
Lys Thr Leu Ser Val Asn Lys Ser Asp Val Ser Leu Asp Leu Val Asn
             20                  25                  30 gaa ata gct aaa tat cca gat ttt tta aca atg gct aat gat gtg tat   144
Glu Ile Ala Lys Tyr Pro Asp Phe Leu Thr Met Ala Asn Asp Val Tyr
         35                  40                  45 ggc gat tct tgc ttt ttt ttt gcc agg aga gaa caa tgt tat gct aga   192
Gly Asp Ser Cys Phe Phe Phe Ala Arg Arg Glu Gln Cys Tyr Ala Arg
     50                  55                  60 cat tat ttt act aga gga gga gct gtg ggt gat gct ata cct gat aca   240
```

```
                                                                              288
aca act aat caa gat cac aaa tac tat cta gca cct aag agt gga caa
Thr Thr Asn Gln Asp His Lys Tyr Tyr Leu Ala Pro Lys Ser Gly Gln
            85                  90                  95

336
tcc caa agt cct ttg ggt aat tct att tac tat ccc acc gtt agt ggc
Ser Gln Ser Pro Leu Gly Asn Ser Ile Tyr Tyr Pro Thr Val Ser Gly
        100                 105                 110

384
tcc tta gtt tct tct gat gca cag ctc ttt aac aga ccc ttc tgg ttg
Ser Leu Val Ser Ser Asp Ala Gln Leu Phe Asn Arg Pro Phe Trp Leu
    115                 120                 125

413
aaa cgt gca cag ggg cac aat aac ggc at
Lys Arg Ala Gln Gly His Asn Asn Gly
130                 135

<210> SEQ ID NO 29
<211> LENGTH: 137
<212> TYPE: PRT
<213> ORGANISM: Papilloma virus

<400> SEQUENCE: 29

Ile Glu Asp Gly Asp Met Ile Asp Ile Gly Phe Gly Asn Ile Asn Asn
 1               5                  10                  15

Lys Thr Leu Ser Val Asn Lys Ser Asp Val Ser Leu Asp Leu Val Asn
            20                  25                  30

Glu Ile Ala Lys Tyr Pro Asp Phe Leu Thr Met Ala Asn Asp Val Tyr
        35                  40                  45

Gly Asp Ser Cys Phe Phe Phe Ala Arg Arg Glu Gln Cys Tyr Ala Arg
    50                  55                  60

His Tyr Phe Thr Arg Gly Gly Ala Val Gly Asp Ala Ile Pro Asp Thr
65                  70                  75                  80

Thr Thr Asn Gln Asp His Lys Tyr Tyr Leu Ala Pro Lys Ser Gly Gln
                85                  90                  95

Ser Gln Ser Pro Leu Gly Asn Ser Ile Tyr Tyr Pro Thr Val Ser Gly
            100                 105                 110

Ser Leu Val Ser Ser Asp Ala Gln Leu Phe Asn Arg Pro Phe Trp Leu
        115                 120                 125

Lys Arg Ala Gln Gly His Asn Asn Gly
    130                 135

<210> SEQ ID NO 30
<211> LENGTH: 413
<212> TYPE: DNA
<213> ORGANISM: Papilloma virus

<400> SEQUENCE: 30
atgccgttat tgtgcccctg tgcacgtttc aaccagaagg gtctgttaaa gagctgtgca      60
tcagaagaaa ctaaggagcc actaacggtg ggatagtaaa tagaattacc caaaggactt     120
tgggattgtc cactcttagg tgctagatag tatttgtgat cttgattagt tgttgtatca     180
ggtatagcat cacccacagc tcctcctcta gtaaataat gtctagcata acattgttct      240
ctcctggcaa aaaaaaagca agaatcgcca tacacatcat tagccattgt taaaaaatct     300
ggatatttag ctatttcatt tactaaatct aaactaacat ctgatttgtt tactgataat     360
gtcttgttat ttatattgcc aaacccaata tcgatcatat caccgtcctc aat            413

<210> SEQ ID NO 31
<211> LENGTH: 404
```

```
<212> TYPE: DNA
<213> ORGANISM: Papilloma virus
<220> FEATURE:
<221> NAME/KEY: CDS
<222> LOCATION: (1)...(402)

<400> SEQUENCE: 31 ata cag gat ggg gac atg ttt gat ata ggt ttt ggt aat att aac aat      48
Ile Gln Asp Gly Asp Met Phe Asp Ile Gly Phe Gly Asn Ile Asn Asn
 1               5                  10                  15 aaa act cta tct tat aat aag tct gat gta agt tta gac att gtt aat      96
Lys Thr Leu Ser Tyr Asn Lys Ser Asp Val Ser Leu Asp Ile Val Asn
             20                  25                  30 gaa gta tgc aaa tat cca gat ttt ttg aca atg tct aat gat gtg tat     144
Glu Val Cys Lys Tyr Pro Asp Phe Leu Thr Met Ser Asn Asp Val Tyr
         35                  40                  45 gga gac gca tgc ttt tac tgt gcc cga aga gag caa tgt tat gct aga     192
Gly Asp Ala Cys Phe Tyr Cys Ala Arg Arg Glu Gln Cys Tyr Ala Arg
     50                  55                  60 cat tat ttt gtt cgg gga ggt cag gtt gga gat gca ata cct gac gag     240
His Tyr Phe Val Arg Gly Gly Gln Val Gly Asp Ala Ile Pro Asp Glu
 65                  70                  75                  80 gca gtc caa caa gat cac aaa tat tat tta cct tct gat aca cgg cgc     288
Ala Val Gln Gln Asp His Lys Tyr Tyr Leu Pro Ser Asp Thr Arg Arg
                 85                  90                  95 act tta gaa aac tcc acc tat ttt ccc acc gta agc ggg tcg ttg gtg     336
Thr Leu Glu Asn Ser Thr Tyr Phe Pro Thr Val Ser Gly Ser Leu Val
            100                 105                 110 acc tct gat gcc caa cta ttt aat agg ccc ttt tgg tta aaa cgt gca     384
Thr Ser Asp Ala Gln Leu Phe Asn Arg Pro Phe Trp Leu Lys Arg Ala
        115                 120                 125 caa ggc cac aat aac gga at                                          404
Gln Gly His Asn Asn Gly
    130

<210> SEQ ID NO 32
<211> LENGTH: 134
<212> TYPE: PRT
<213> ORGANISM: Papilloma virus

<400> SEQUENCE: 32

Ile Gln Asp Gly Asp Met Phe Asp Ile Gly Phe Gly Asn Ile Asn Asn
 1               5                  10                  15

Lys Thr Leu Ser Tyr Asn Lys Ser Asp Val Ser Leu Asp Ile Val Asn
             20                  25                  30

Glu Val Cys Lys Tyr Pro Asp Phe Leu Thr Met Ser Asn Asp Val Tyr
         35                  40                  45

Gly Asp Ala Cys Phe Tyr Cys Ala Arg Arg Glu Gln Cys Tyr Ala Arg
     50                  55                  60

His Tyr Phe Val Arg Gly Gly Gln Val Gly Asp Ala Ile Pro Asp Glu
 65                  70                  75                  80

Ala Val Gln Gln Asp His Lys Tyr Tyr Leu Pro Ser Asp Thr Arg Arg
                 85                  90                  95

Thr Leu Glu Asn Ser Thr Tyr Phe Pro Thr Val Ser Gly Ser Leu Val
            100                 105                 110

Thr Ser Asp Ala Gln Leu Phe Asn Arg Pro Phe Trp Leu Lys Arg Ala
        115                 120                 125

Gln Gly His Asn Asn Gly
    130
```

```
<210> SEQ ID NO 33
<211> LENGTH: 404
<212> TYPE: DNA
<213> ORGANISM: Papilloma virus

<400> SEQUENCE: 33
attccgttat tgtggccttg tgcacgtttt aaccaaaagg gcctattaaa tagttgggca      60
tcagaggtca ccaacgaccc gcttacggtg ggaaaatagg tggagttttc taaagtgcgc     120
cgtgtatcag aagtaaata atatttgtga tcttgttgga ctgcctcgtc aggtattgca      180
tctccaacct gacctccccg aacaaaataa tgtctagcat aacattgctc tcttcgggca     240
cagtaaaagc atgcgtctcc atacacatca ttagacattg tcaaaaaatc tggatatttg     300
catacttcat taacaatgtc taaacttaca tcagacttat tataagatag agttttattg     360
ttaatattac caaaacctat atcaaacatg tccccatcct gtat                     404
```

US 6,413,522 B1

PAPILLOMA VIRUSES, PRODUCTS FOR THE DETECTION THEREOF AS WELL AS FOR TREATING DISEASES CAUSED BY THEM

This is a national phase filing of the Application No. PCT/DE97/02659, which was filed with the Patent Corporation Treaty on Nov. 12, 1997, and is entitled to priority of the German Patent Application DE 196 48 962.8, filed Nov. 26, 1996.

I. FIELD OF THE INVENTION

This invention relates to a DNA coding for a peptide of a papilloma virus major capsid protein and a papilloma virus genome, respectively. In addition, this invention concerns proteins coded by the papilloma virus genome and antibodies directed against them as well as their use for diagnosis, treatment and vaccination.

II. BACKGROUND OF THE INVENTION

It is known that papilloma viruses infect the epithelium of human beings and animals. Human papilloma viruses (hereinafter referred to as HP viruses) are found in benign epithelial neoplasms, e.g. warts, condylomas in the genital zone, and malignant epithelial neoplasms, e.g. carcinomas of the skin and the uterus (zur Hausen, 1996, *Biochimica et Biophysica Acta* (*BBA*) 1288:55–78). HP viruses are also considered for the growth of malignant tumors in the oropharyngeal zone (zur Hausen, 1977, *Curr. Top. Microbiol. Immunol.* 78:1–30).

Papilloma viruses have an icosahedral capsid without envelope in which a circular, double-stranded DNA molecule of about 7900 bp is present. The capsid comprises a major capsid protein (L1) and a minor capsid protein (L2). Both proteins, coexpressed or L1 expressed alone, result in vitro in the formation of virus-like particles (Kirnbauer et al., 1993, *Journal of Virology* 67:6929–6936).

Papilloma viruses cannot be proliferated in monolayer cell culture. Therefore, their characterization is extremely difficult, the detection of papilloma viruses already creating considerable problems. This applies especially to papilloma viruses in carcinomas of the skin.

Thus, it is the object of the present invention to provide a product by which papilloma viruses can be detected, particularly in carcinomas of the skin. Furthermore, a product should be provided to be able to take therapeutic steps against these papilloma viruses.

According to the invention, this is achieved by providing the subject matters in the claims.

III. SUMMARY OF THE INVENTION

This invention relates to a DNA coding for a peptide of a papilloma virus major capsid protein and a papilloma virus genome, respectively. Furthermore, this invention concerns proteins coded by the papilloma virus genome and antibodies directed thereagainst as well as the use thereof for diagnosis, treatment and vaccination.

IV. BRIEF DESCRIPTION OF THE DRAWINGS

FIG. 1 shows the base sequence (SEQ ID NOS:1 and 3) and the amino acid sequence (SEQ ID NO:2), derived therefrom, of a DNA coding for a peptide of L1 of a papilloma virus. This DNA was deposited as plasmid DL17 with DSM (*Deutsche Sammlung von Mikroorganismen und Zellkulturen* (German-type collection of micro-organisms and cell cultures)) under DSM 11180 on Sep. 17, 1996.

FIG. 2 shows the base sequence (SEQ ID NOS:4 and 6) and the amino acid sequence (SEQ ID NO:5), derived therefrom, of a DNA coding for a peptide of L1 of a papilloma virus. This DNA was deposited as plasmid DL20 with DSM under DSM 11181 on Sep. 17, 1996.

FIG. 3 shows the base sequence (SEQ ID NOS:7 and 9) and the amino acid sequence (SEQ ID NO:8), derived therefrom, of a DNA coding for a peptide of L1 of a papilloma virus. This DNA was deposited as plasmid DL27 with DSM under DSM 11182 on Sep. 17, 1996.

FIG. 4 shows the base sequence (SEQ ID NOS:10 and 12) and the amino acid sequence (SEQ ID NO:11), derived therefrom, of a DNA coding for a peptide of L1 of a papilloma virus. This DNA was deposited as plasmid D135 with DSM under DSM 11183 on Sep. 17, 1996.

FIG. 5 shows the base sequence (SEQ ID NOS:13 and 15) and the amino acid sequence (SEQ ID NO:14), derived therefrom, of a DNA coding for a peptide of L1 of a papilloma virus. This DNA was deposited as plasmid DL40 with DSM under DSM 11184 on Sep. 17, 1996.

FIG. 6 shows the base sequence (SEQ ID NOS:16 and 18) and the amino acid sequence (SEQ ID NO:17), derived therefrom, of a DNA coding for a peptide of L1 of a papilloma virus. This DNA was deposited as plasmid DL78 with DSM under DSM 11185 on Sep. 17, 1996.

FIG. 7 shows the base sequence (SEQ ID NOS:19 and 21) and the amino acid sequence (SEQ ID NO:20), derived therefrom, of a DNA coding for a peptide of L1 of a papilloma virus. This DNA was deposited as plasmid DL82 with DSM under DSM 11186 on Sep. 17, 1996.

FIG. 8 shows the base sequence (SEQ ID NOS:22 and 24) and the amino acid sequence (SEQ ID NO:23), derived therefrom, of a DNA coding for a peptide of L1 of a papilloma virus. This DNA was deposited as plasmid DL83 with DSM under DSM 11187 on Sep. 17, 1996.

FIG. 9 shows the base sequence (SEQ ID NOS:25 and 27) and the amino acid sequence (SEQ ID NO:26), derived therefrom, of a DNA coding for a peptide of L1 of a papilloma virus. This DNA was deposited as plasmid DL84 with DSM under DSM 11188 on Sep. 17, 1996.

FIG. 10 shows the base sequence (SEQ ID NOS:28 and 30) and the amino acid sequence (SEQ ID NO:29), derived therefrom, of a DNA coding for a peptide of L1 of papilloma virus. This DNA was deposited as plasmid DL100 with DSM under DSM 11189 on Sep. 17, 1996.

FIG. 11 shows the base sequence (SEQ ID NOS:31 and 33) and the amino acid sequence (SEQ ID NO:32), derived therefrom, of a DNA coding for a peptide of L1 of a papilloma virus. This DNA was deposited as plasmid HR22 with DSM under DSM 11190 on Sep. 17, 1996.

V. DETAILED DESCRIPTION OF THE INVENTION

The subject matter of the invention relates to a DNA coding for a peptide of a papilloma virus major capsid protein (L1), the peptide comprising the amino acid sequence of FIG. 1 (SEQ ID NO:2), FIG. 2 (SEQ ID NO:5), FIG. 3 (SEQ ID NO:8), FIG. 4 (SEQ ID NO:11), FIG. 5 (SEQ ID NO:14), FIG. 6 (SEQ ID NO:17), FIG. 7 (SEQ ID NO:20), FIG. 8 (SEQ ID NO:23), FIG. 9 (SEQ ID NO:26), FIG. 10 (SEQ ID NO:29) or FIG. 11 (SEQ ID NO:32) or an amino acid sequence differing therefrom by one or more amino acids.

A further subject matter of the invention relates to a DNA coding for a peptide of a papilloma virus major capsid protein, the DNA comprising the base sequence of FIG. 1 (SEQ ID NOS:1 and 3), FIG. 2 (SEQ ID NOS:4 and 6), FIG. 3 (SEQ ID NOS:7 and 9), FIG. 4 (SEQ ID NOS:10 and 12), FIG. 5 (SEQ ID NOS:13 and 15), FIG. 6 (SEQ ID NOS:16 and 18), FIG. 7 (SEQ ID NOS:19 and 21), FIG. 8 (SEQ ID NOS:22 and 24), FIG. 9 (SEQ ID NOS:25 and 27), FIG. 10 (SEQ ID NOS:28 and 30) or FIG. 11 (SEQ ID NOS:31 and 33) or a base sequence differing therefrom by one or more base pairs.

The above DNA was compared with the DNA of known papilloma viruses. Sequence homology studies were carried out. A homology having less than 90% shows that a DNA according to the invention is a new HP virus. The DNAs according to the invention have the following sequence homologies with respect to known papilloma viruses:
DNA of FIG. 1: 67% with respect to HP virus 65
DNA of FIG. 2: 62% with respect to HP virus 17
DNA of FIG. 3: 78% with respect to HP virus 65
DNA of FIG. 4: |
DNA of FIG. 5: 86% with respect to HP virus 10
DNA of FIG. 6: 86% with respect to HP virus 10
DNA of FIG. 7; 62% with respect to HP virus 8
DNA of FIG. 8: 66% with respect to HP virus 65
DNA of FIG. 9: 64% with respect to HP virus 65
DNA of FIG. 10: 75% with respect to HP virus 15
DNA of FIG. 11: 81% with respect to HP virus 22 and 23, respectively.

According to the invention, the above DNA can be present in a vector and expression vector, respectively. A person skilled in the art is familiar with examples thereof. In the case of an expression vector for *E. coli* these are e.g. pGEMEX, pUC derivatives, pGEM-T and pGEX-2T. For the expression in yeast e.g. pY100 and Ycpad1 have to be mentioned, while for the expression in animal cells e.g. pKCR, pEF-BOS, cDM8 and pCEV4 have to be indicated.

The person skilled in the arts knows suitable cells to express the above DNA present in an expression vector. Examples of such cells comprise the *E. coli* strains HB101, DH1, x1776, JM101, JM109, and XL1-Blue, the yeast strain *Saccharomyces cerevisiae* and the animal cells L, NH-3T3, FM3A, CHO, COS, Vero, and HeLa.

The person skilled in the art knows in which way the above DNA has to be inserted in an expression vector. He is also familiar with the fact that the above DNA can be inserted in connection with a DNA coding for another protein and peptide, respectively, so that the above DNA can be expressed in the form of a fusion protein.

A further subject matter of the invention relates to a papilloma virus genome which comprises the above DNA. The expression "papilloma virus genome" also comprises an incomplete genome, i.e. fragments of a papilloma virus genome, which comprise the above DNA. This may be e.g. a DNA coding for L1 or a portion thereof.

A common process can be used for the provision of the above papilloma virus genome. It is favorable to use a process which comprises the following processing steps:
(a) isolation of the total DNA from a biopsy of epithelial neoplasm,
(b) hybridization of the total DNA of (a) with the above DNA so as to detect a papilloma virus genome included in the total DNA of (a), and
(c) cloning of the total DNA of (a) containing the papilloma virus genome, in a vector and optionally subcloning the resulting clone, all processing steps originating from common DNA recombination technique.

As far as the isolation, hybridization and cloning of cell DNA is concerned, reference is made by way of supplement to Sambrook et al., *Molecular Cloning, A Laboratory Manual,* second edition, Cold Spring Harbor Laboratory (1989).

The expression "epithelial neoplasm" comprises any neoplasms of epithelium in man and animal. Examples of such neoplasms are warts, condylomas in the genital zone and carcinomas of the skin. The latter are used preferably to isolate the above papilloma virus genome.

The expression "vector" comprises any vectors suitable for cloning chromosomal DNA and extra chromosomal DNA, respectively. Examples of such vectors are cosmids such as pWE15 and Super Cos1, and phages such as λ-phages, e.g. λZAP expressvector, λZAPII vector and λgt10 vector. In the present case, λ-phages are used preferably. The above vectors are known and obtainable from the company of Stratagene.

Papilloma virus genomes according to the invention may be present in integrated form in chromosomal DNA or in extra chromosomal fashion. The person skilled in the art is familiar with processes serving the clarification thereof. He also knows processes serving for finding out the optimum restriction enzymes for cloning the papilloma virus genomes. He will orient himself by genomes of known papilloma viruses. In particular, the person skilled in the art will pay corresponding attention to the above-mentioned HP viruses.

The provision of a papilloma virus genome referred to as DL17-G is described by way of example. For this purpose, the total DNA is isolated from a biopsy of a squamous cell carcinoma, cleaved by BamHI and separated electrophoretically in an agarose gel. The agarose gel is then subjected to a blotting method so as to transfer the DNA to a nitrocellulose membrane. It is inserted in a hybridization method in which the DNA of FIG. 1 is used as labeled sample, optionally in combination with a DNA of HP virus 65. Hybridization with the papilloma virus DNA present in the total DNA is obtained.

Moreover, the above total DNA cleaved by BamHI is cloned in a λ-phage. The corresponding clones, i.e. the clones containing the papilloma virus DNA are identified by hybridization with the DNA of FIG. 1, optionally in combination with a DNA of the HP virus 65. The insert of these clones is then subjected to a further cloning in a plasmid vector so as to obtain a clone which contains the papilloma virus genome DL17-G. The genome is confirmed by sequencing.

Further papilloma virus genomes are provided analogously. They are designated in accordance with the DNAs used for their provision, namely by: DL20-G, DL27-G, DL35-G, DL40-G, DL78-G, DL82-G, DL-83G, DL84-G, DL100-G and HR22-G, respectively.

A further subject matter of the invention relates to a protein which is coded by the above papilloma virus genome. Such a protein is e.g. a major capsid protein (L1) or a minor capsid protein (L2). An above protein is prepared as usual. The preparation of L1 and L2, respectively, of the papilloma virus genome DL17-G is described by way of example. For this purpose, the HP virus 65 related to the DNA of FIG. 1 (SEQ ID NOS:1 and 3) is used. The full sequence and the position of individual DNA regions coding for proteins are known in connection therewith. These DNAs are identified on the papilloma virus genome DL17-G by parallel restriction cleavages of both genomes and subsequent hybridization with various fragments concerning the DNA encoding L1 and L2, respectively. They are confirmed by sequencing. The DNA coding for L1 is referred to as DL17-G-L1 DNA and the DNA coding for L2 is referred to as DL17-G-L2 DNA.

Furthermore, the DNA coding for L1 and L2, respectively, is inserted in an expression vector. Examples thereof are mentioned above for *E. coli,* yeast and animal cells. In particular, reference is made to the vector pGEX-2T as regards the expression in *E. coli* (Kirnbauer et al., supra). Having inserted the DL17-G-L1 DNA and DL17-G-L2 DNA, one obtains pGEX-2T-DL17-G-L1 and pGEX-2T-DL17-G-L2, respectively. After transforming *E. coli,* these expression vectors express a glutathione S transferase L1 fusion protein and glutathione S transferase L2 fusion protein, respectively. The proteins are purified as usual.

The bacculovirus system and vaccinia virus system, respectively, is mentioned for a further expression of the above DNA encoding L1 and L2, respectively. Expression vectors usable for this purpose are e.g. pEV mod. and pSynwtVI⁻ for the bacculovirus system (Kirnbauer et al., supra). Especially vectors with the vaccinia virus "early" (p7.5k) promoter and "late" (Psynth, p11K) promoter, respectively, have to be mentioned for the vaccinia virus system (Hagensee et al., 1993, *Journal of Virology* 67:315–322). The bacculovirus system is preferred in the present case. Having inserted the above DNA encoding L1 and L2, respectively, in pEV mod., one obtains pEVmod.-DL17-G-L1 and pEVmod.-DL17-C-L2, respectively.

The former expression vector as such or both expression vectors jointly lead to the formation of virus-like particles after infection of SF-9 insect cells. In the former case, such a particle comprises an L1 protein, while in the latter case it contains an L2 protein in addition to an L1 protein.

A virus-like particle of the latter case is also obtained by inserting the above DL17-G-L1 and DL17-G-L2 DNAs jointly in the expression vector pSynwtVI⁻ and using the resulting pSynwtVI⁻DL17-G-L1/L2 for the infection of SF-9 insect cells. The above virus-like particles are purified as usual. They also represent a subject matter of the invention.

A further subject matter of the invention relates to an antibody directed against an above protein and virus-like particle, respectively. The preparation thereof is made as usual. It is described by way of example for the preparation of an antibody which is directed against a virus-like particle comprising L1 of DL17-G. For this purpose, the virus-like particle is injected subcutaneously into BALB/c mice. This injection is repeated at intervals of 3 weeks each. About 2 weeks after the last injection, the serum containing the antibody is isolated and tested as usual.

In a preferred embodiment, the antibody is a monoclonal antibody. For its preparation, spleen cells are removed from the mice after the above fourth injection and fused with myeloma cells as usual. The further cloning also takes place according to known methods.

By means of the present invention it is possible to detect papilloma viruses, particularly in carcinomas of the skin. For this purpose, the DNA according to the invention can be used as such or when comprised by a further DNA. The latter may also be a papilloma virus genome or a portion thereof.

The present invention also enables the provision of formerly unknown papilloma viruses. They are found especially in carcinomas of the skin. In addition, the invention supplies proteins and virus-like particles which originate from these papilloma viruses. Moreover, antibodies are provided which are directed against these proteins and particles, respectively.

The present invention also enables to take diagnostic and therapeutic steps in the case of papilloma virus diseases. Moreover, it supplies the possibility of building up a vaccine against papilloma virus infections. Thus, the present invention represents a break-through in the field of papilloma virus research.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VI. EXAMPLES

A. Example 1

Identification of the Papilloma Virus Genome DL17-G

The total DNA is isolated from a biopsy of a squamous cell carcinoma. 10 µg of this DNA are cleaved by the restriction enzyme BamHI and separated electrophoretically in a 0.5% agarose gel. At the same time, 10 µg of the above DNA which was not cleaved, is also separated. The agarose gel is subjected to a blotting method so as to transfer the DNA from the agarose gel to a nitrocellulose membrane. It is employed in a hybridization method in which the above DNA of FIG. 1 (SEQ ID NOS:1 and 3) is used in combination with the HP virus-65 DNA as $p^{32}$-labeled sample. Hybridization with the blotted DNA is obtained.

The person skilled in the field of DNA recombination technique is familiar with the above methods. Reference is made to Sambrook et al., supra, by way of supplement.

B. Example 2

Cloning of the Papilloma Virus Genome DL17-G

The biopsy DNA obtained from Example 1 is cleaved by the restriction enzyme BamHI. The resulting fragments are used in a ligase reaction in which the dephosphorylated vector λZAP express cleaved by BamHI is also present. The resulting recombinant DNA molecules are packed in bacteriophages, and they are used for infecting bacteria. For these processing steps, the ZAP express vector kit offered by the company of Stratagene is used. The resulting phage plaques are then subjected to a hybridization process which uses the $p^{32}$-labeled DNA of FIG. 1 (SEQ ID NOS:1 and 3) employed in Example 1 in combination with $p^{32}$-labeled HP virus-65 DNA. Hybridization with corresponding phage plaques is obtained. The BamHI fragments of DL17-G are isolated therefrom and used in a further ligase reaction together with a BamHI-cleaved, dephosphorylated plasmid vector, pBluescript. The resulting recombinant DNA molecules are used for transforming bacteria, *E. coli* XL1-Blue. By restriction cleavages and hybridization with the above DNA samples, respectively, a bacterial clone containing the papilloma virus genome DL17-G is identified. The plasmid of this bacterial clone is referred to as pBlue-DL17-G.

All references cited within the body of the instant specification are hereby incorporated by reference in their entirety.

What is claimed is:

1. An isolated polynucleotide consisting essentially of:
   (a) a nucleotide sequence encoding the peptide of SEQ ID NO:2, SEQ ID NO:5, or SEQ ID NO:8;
   (b) a nucleotide sequence hybridizing to the nucleotide sequence of SEQ ID NO:1, SEQ ID NO:4, or SEQ ID NO:7; or
   (c) the complement of (a) or (b);
   wherein the polynucleotide has a homology of at least 90% to the nucleotide sequence of SEQ ID NO:1, SEQ ID NO:4, or SEQ ID NO:7, or the complement thereof.

2. An isolated polynucleotide encoding a peptide of a papilloma virus major capsid protein, wherein the said polynucleotide has been obtained using the following steps:
   (a) incubating total DNA isolated from a biopsy of epithelial neoplasm with a nucleic acid having at least a portion of the nucleotide sequence of SEQ ID NO:1, SEQ ID NO:4, or SEQ ID NO:7, under a condition that allows hybridization of a polynucleotide derived from a papilloma virus genome included in the total DNA to said nucleotide sequence of the complement of SEQ ID NO:1, SEQ ID NO:4, or SEQ ID NO:7; and
   (b) identifying and isolating a polynucleotide that hybridizes to the complement of the nucleotide sequence of SEQ ID NO:1, SEQ ID NO:4, or SEQ ID NO:7 in step (a);
   wherein the polynucleotide has a homology of at least 90% to the nucleotide sequence of SEQ ID NO:1, SEQ ID NO:4, or SEQ ID NO:7.

3. An isolated polynucleotide, consisting essentially of (a) a nucleic acid encoding a peptide comprising the amino acid sequence of SEQ ID NO:2, SEQ ID NO:5, or SEQ ID NO:8, or (b) the complement of (a).

4. An isolated polynucleotide, wherein the polynucleotide consists essentially of the nucleotide sequence of SEQ ID NO:1, SEQ ID NO:4, or SEQ ID NO:7, or the complement thereof.

5. A plasmid comprising the polynucleotide of claim 1 or 2.

6. A plasmid comprising the polynucleotide of claim 3 or 4.

7. An expression vector comprising the polynucleotide of claim 1 or 2.

8. An expression vector comprising the polynucleotide of claim 3 or 4.

9. A host cell comprising the plasmid of claim 5.

10. A host cell comprising the plasmid of claim 6.

11. A host cell comprising the expression vector of claim 9.

12. A host cell comprising the expression vector of claim 8.

13. A method of producing a peptide of a papilloma virus major capsid protein, comprising cultivating the host cell of claim 11 under suitable conditions.

14. A method of producing a peptide of a papilloma virus major capsid protein, comprising cultivating the host cell of claim 12 under suitable conditions.

15. A method of detecting a papilloma virus DNA, comprising:
   (a) hybridizing under stringent conditions at least a portion of the polynucleotide of claim 1, 2, 3, or 4 to a DNA sample; and
   (b) identifying papilloma virus in said DNA sample by detecting a hybridization signal.

16. A composition comprising the polynucleotide of claim 1, 2, 3, or 4 as reagent for diagnosis and a diagnostically acceptable carrier.

17. A method of producing a papilloma virus genome, comprising:
   (a) incubating total DNA isolated form a biopsy of epithlial neoplasm with a nucleic acid having at least a portion of the nucleotide sequence of SEQ ID NO:1, SEQ ID NO:4, or SEQ ID NO:7, under a condition that allows hybridization of a polynucleotide derived from a papilloma virus genome included in the total DNA to said nucleotide sequence of the complement of SEQ ID NO:1, SEQ ID NO:4, or SEQ ID NO:7; and
   (b) identifying and isolating a polypnucleotide that hybridizes to the nucleotide sequence of the complement of SEQ ID NO:1, SEQ ID NO:4, or SEQ ID NO:7 in step (a).

18. The method of claim 17, wherein the polypnucleotide has a homology of at least 90% to the nucleotide sequence of SEQ ID NO:1, SEQ ID NO:4, or SEQ ID NO:7.

19. A composition comprising the polynucleotide of claim 1, 2, 3, or 4 as reagent for vaccination and a pharmaceutically acceptable carrier.

20. A method of vaccinating a subject in need against papilloma virus, comprising administering to said subject the composition of claim 19.

21. A method of diagnosing a condition caused by papilloma virus in a subject in need, comprising exposing said subject the composition of claim 16.

22. A method of using the polynucleotide of claim 1, 2, 3, or 4 as reagent for diagnosis.

23. The method according to claim 22, wherein the diagnosis concerns papilloma virus infections or diseases.

* * * * *